(12) United States Patent
Behrens et al.

(10) Patent No.: US 10,179,905 B2
(45) Date of Patent: *Jan. 15, 2019

(54) FACTOR VII CONJUGATES

(71) Applicant: Novo Nordisk Health Care AG, Zurich (CH)

(72) Inventors: Carsten Behrens, Koebenhavn (DK); Henrik Oestergaard, Oelstykke (DK); Henning Ralf Stennicke, Kokkedal (DK)

(73) Assignee: Novo Nordisk Health Care AG, Zurich (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/453,188

(22) Filed: Mar. 8, 2017

(65) Prior Publication Data

US 2017/0355974 A1 Dec. 14, 2017

Related U.S. Application Data

(63) Continuation of application No. 14/433,151, filed as application No. PCT/EP2013/071499 on Oct. 15, 2013.

(60) Provisional application No. 61/715,929, filed on Oct. 19, 2012.

(30) Foreign Application Priority Data

Oct. 15, 2012 (EP) ..................... 12188472

(51) Int. Cl.
*C12N 9/64* (2006.01)
*C12N 9/96* (2006.01)
*A61K 38/48* (2006.01)
*A61K 47/61* (2017.01)

(52) U.S. Cl.
CPC ........ *C12N 9/6437* (2013.01); *A61K 38/4846* (2013.01); *A61K 47/61* (2017.08); *C12N 9/96* (2013.01); *C12Y 304/21021* (2013.01)

(58) Field of Classification Search
CPC .. A61K 38/4846; A61K 47/61; C12N 9/6437; C12N 9/96; C12Y 304/21021
See application file for complete search history.

(56) References Cited

U.S. PATENT DOCUMENTS

| | | | |
|---|---|---|---|
| 6,806,063 B2 | 10/2004 | Pedersen et al. | |
| 7,371,543 B2 | 5/2008 | Pedersen et al. | |
| 7,511,024 B2 | 3/2009 | Pedersen et al. | |
| 7,517,974 B2 | 4/2009 | Pedersen et al. | |
| 8,486,892 B2* | 7/2013 | Dorwald ............. | A61K 9/0019 514/14.3 |
| 9,370,583 B2* | 6/2016 | Oestergaard ... | C12Y 304/21021 |
| 9,371,370 B2* | 6/2016 | Oestergaard ... | C12Y 304/21021 |
| 2003/0044908 A1 | 3/2003 | Persson | |
| 2006/0040856 A1 | 2/2006 | DeFrees et al. | |
| 2009/0291890 A1 | 11/2009 | Madison et al. | |
| 2010/0036001 A1 | 2/2010 | DeAngelis | |
| 2012/0093840 A1 | 4/2012 | Ostergaard et al. | |
| 2013/0004524 A1 | 1/2013 | Buchardt et al. | |
| 2013/0040888 A1 | 2/2013 | Peschke et al. | |
| 2015/0105321 A1 | 4/2015 | Oestergaard et al. | |
| 2015/0225711 A1* | 8/2015 | Behrens ............. | C12N 9/6437 424/94.3 |
| 2015/0259665 A1* | 9/2015 | Behrens ......... | C12Y 304/21021 424/94.3 |
| 2015/0307865 A1* | 10/2015 | Stennicke .......... | A61K 38/4846 424/94.64 |
| 2016/0120992 A1 | 5/2016 | Oestergaard et al. | |
| 2017/0096655 A1* | 4/2017 | Oestergaard ......... | C12N 9/6437 |

FOREIGN PATENT DOCUMENTS

| | | |
|---|---|---|
| WO | 0158935 A2 | 8/2001 |
| WO | 02/22776 A2 | 3/2002 |
| WO | 03031464 A2 | 4/2003 |
| WO | 2005/014035 A2 | 2/2005 |
| WO | 2005/075635 A2 | 8/2005 |
| WO | 2006/127896 A2 | 11/2006 |
| WO | 2006/134174 A2 | 12/2006 |
| WO | 2007022512 A2 | 2/2007 |
| WO | 2007/031559 A2 | 3/2007 |
| WO | 2008/025856 A2 | 3/2008 |
| WO | 2008/074032 A1 | 6/2008 |
| WO | 2008127702 A2 | 10/2008 |
| WO | 2009126307 A2 | 10/2009 |
| WO | 2010/030342 A2 | 3/2010 |
| WO | 2011092242 A1 | 8/2011 |
| WO | 2011101277 A1 | 8/2011 |
| WO | 2012/007324 A2 | 1/2012 |
| WO | 2012035050 A2 | 3/2012 |
| WO | 2014/060401 A1 | 4/2014 |

(Continued)

OTHER PUBLICATIONS

Fenaille et al. Mass spectrometric characterization of N- and O-glycans of plasma-derived coagulation factor VII. Glycoconj J, 2008. vol. 25, pp. 827-842. (Year: 2008).*

DeAngelis P L "HEPtune: A process of conjugating a Naturally occurring sugar molecule, Heparosan to a drug for enhanced drug delivery", Journal: Drug Development & Delivery, Year Jan. 1, 2013 (Jan. 1, 2013), pp. 1-4, XP002691459, Retrieved from the Internet.

Ditte M Karpf et al: "Prolonged half-life of glycoPEGylated rFVIIa variants compared to native rFVIIa".Journal :Thrombosis Research,Year Aug. 1, 2011 vol. 128. No. 2, pp. 191-195,XP002691140.

Dufner G et al.Base- and Sugar-Modified Cytidine Monophosphate N-Acetylneuraminic Acid (CMP-Neu5Ac) Analogues—Synthesis and Studies with alpha(2-6)-Sialyltransferase from Rat Liver. Journal Eur. J. Org. Chem Year 2000,pp. 1467-1482 XP055124461.

(Continued)

*Primary Examiner* — Marcela M Cordero Garcia
(74) *Attorney, Agent, or Firm* — Knobbe Martens Olson & Bear LLP

(57) ABSTRACT

The present invention relates to the conjugation of Factor VII polypeptides with heparosan polymers. The resultant conjugates may be used to deliver Factor VII, for example in the treatment or prevention of bleeding disorders.

14 Claims, 7 Drawing Sheets

(56) References Cited

FOREIGN PATENT DOCUMENTS

| WO | 2014060397 A1 | 4/2014 |
|---|---|---|
| WO | 2014140103 A2 | 9/2014 |

OTHER PUBLICATIONS

Malmstrom J, Characterization of 40 kDa poly(ethylene glycol) polymers by proton transfer reaction QTOF mass spectrometry and 1H-NMR spectroscopy, Analytical Bioanalytical Chemistry, Year2012, vol. 403, pp. 1167-1177.
Stennicke H. R et al.A novel B-domain O-glycoPEGylated FVIII (N8-GP) demonstrates full efficacy and prolonged effect in hemophilic mice models, Journal : Blood, Year 2013, vol. 121 Issue11, pp. 2108-2016.
Stennicke HR et al.Generation and biochemical characterization of glycoPEGylated factor VIIa derivatives, Journal :Thrombosis Haemostatis, Year 2008, vol. 100, Issue 5 pp. 920-928.
Agersø.H. et al., Recombinant human factor VIIa (rFVIIa) cleared principally by antithrombin following intravenous administration in hemophilia patients. J. Thromb. Haemost. vol. 9, No. 2, Year (2011), pp. 333-338.
Database Geneseq [Online]; Jan. 7, 2010 (Jan. 7, 2010),; "Human factor VII (FVII) mutein, SEQ:346.", XP002722258,; retrieved from EBI accession No.; GSP:AXS64259; Database accession No. AXS64259; * sequence *; & WO 2009/126307 A2 (Catalyst Biosciences; Inc [US]; Madison Edwin L [US]; Thanos; Christophe) Oct. 15, 2009 (Oct. 15, 2009).
Database UniProt [Online] Sep. 18, 2013 "RecName: Full= Coagulation factor VII; EC=3.4.21.21; AltName: Full=Serum prothrombin conversion accelerator; Contains: RecName: Full= Factor VII light chain; Contains: RecName: Full=Factor VII heavy chain;", XP002722259.
Database UniProt [Online]; Sep. 18, 2013 (Sep. 18, 2013), "SubName: Full=Uncharacterized protein;", XP002722260,; retrieved from EBI accession No. UNIPROT:G3VNT5, Database accession No. G3VNT5; * sequence *; & W. Miller et al: "Genetic diversity and population structure of the endangered; marsupial *Sarcophilus harrisii* (Tasmanian devil) ", Proceedings of the National Academy of Sciences, vol. 108. No. 30, Year 2011, pp. 12348-12353. XP055109905.; ISSN: 0027-8424. 001: 10. 1073/pnas. 1102838108.
De Paula et al, Recombinant factor VIIa analog (vatreptacog alfa [activated]); for treatment of joint bleeds in hemophilia patients with inhibitors: a randomized controlled trial, Journal of Thrombosis and Haemostasis, 10, Year 2012, pp. 81-89.
DeAngelis Paul L. , HEPtune: A Process of Conjugating a Naturally Occurring Sugar Molecule, Heparosan, to a Drug for Enhanced Drug Delivery, Drug develpment and delivery drug delivery technology, vol. 13, No. 1, Jan. 2013. Retrieved from the internet. ; http://drug-dev.com/Main/Back-Issues/-HEPtune-A-Process-of-Conjugating-a-Naturally-Occu-160.aspx; [retrieved on Oct. 15, 2014].
Ditte M. Karpf et al., Prolonged half-life of glycoPEGylated rFVIIa variants compared to native rFVIIa, Thrombosis Research, vol. 128, No. 2, Year 2011, pp. 191-195.
H. J. Metzner et al., Extending the pharmacokinetic half-life of coagulation factors by fusion to recombinant albumin, Thrombosis and Haemostasis, vol. 110, No. 5, Year 2013, pp. 931-939.
Harvey, SB et al., Mutagenesis of the y-Carboxyglutamic Acid Domain of Human Factor VII to Generate Maximum Enhancement of the Membrane Contact Site. J. Biol. Chem. 278, Year 2003, pp. 8363-8369.
Huntington,J. A., Mechanisms of glycosaminoglycan activation of the serpins in; hemostasis. J. Thromb. Haemost. vol. 1, No. 7, Year 2003, pp. 1535-1549.
Kounnas,M.Z. et al., Cellular internalization and degradation of antithrombin III-thrombin, heparin cofactor II-thrombin, and alpha 1-antitrypsin-trypsin complexes is mediated by the low density lipoprotein receptor-related protein. J. Biol. Chem. vol. 271, No. 11 Year 1996, pp. 6523-6529.
Lollar,P. et al., Clearance of thrombin from circulation in rabbits by; high-affinity binding sites on endothelium. Possible role in the inactivation of thrombin by; antithrombin III., J. Clin. Invest, vol. 66, No. 6, Year 1980, pp. 1222-1230.
Narita,M., et al., The low-density lipoprotein receptor-related protein (LRP) mediates clearance of coagulation factor Xa in vivo. Blood 91, No. 2, Year 1998, pp. 555-560.
Nayak,R.C et al., Endothelial cell protein C receptor cellular localization and trafficking:; potential functional implications. Blood, 114, No. 9, Year 2009, pp. 1974-1986.
Olson,S.T. et al., Accelerating ability of synthetic oligosaccharides on; antithrombin inhibition of proteinases of the clotting and fibrinolytic systems. Comparison; with heparin and low-molecular-weight heparin. Thromb Haemost vol. 92, Year 2004, pp. 929-939.
Persson Egon et al: "Assignment of molecular properties of a superactive coagulation factor VIIa variant to individual amino acid changes" European Journal of Biochemistry, vol. 269, No. 23, Year 2002, pp. 5950-5955.
Rao, L.V. et al., Binding of factor VIIa to tissue factor permits rapid antithrombin III/heparin inhibition of factor VIIa. Blood 81, No. 10, Year 1993, pp. 2600-2607.
Rao, L.V. et al., Regulation of tissue factor-factor VIIa expression on; cell surfaces: a role for tissue factor-factor VIIa endocytosis. Mol. Cell Biochem. vol. 253, No. 1-2,Year 2003, pp. 131-140.
Wildgoose,P. et al., Measurement of basal levels of factor VIIa in hemophilia A and B patients. Blood 80, No. 1, Year 1992, pp. 25-28.
Coagulopathy treatment, from http://www.healthgrades.com/conditions/coagulopathy--treatments, p. 1, accessed Dec. 5, 2014.
Morrissey J. H. et al., Quantitation of Activated Factor VI1 Levels in Plasma Using a Tissue Factor Mutant Selectively Deficient in Promoting Factor VII Activation, Journal: Blood, Year: 1993, vol. 18, No. 3, pp. 734-744.
Karpf D. M. et al., Prolonged half-life of glycoPEGylated rFVIIa variants compared to native rFVIIa, Journal: Thrombosis Research, Year: 2011, vol. 128, pp. 191-195.
Harlan T et al., Caisson Biotech: Innovation in Drug Delivery Using a Naturally Occurring Sugar Molecule, Journal: Drug Development & Delivery, Year: 2012, vol. 12, No. 6, pp. 59-61.
Bouley J. et al., Hustling on Half-lives, Journal: Drug Discovery News, vol. 8, No. 6, Year: 2012, whole document.
Kelsen K., Novo Nordisk, Caisson Biotech announces license agreement, Journal: Drug Discovery News, Year: 2012, the whole document.
DeAngelis P. L., HEPtune: A Process of Conjugating a Naturally Occurring Sugar Molecule, Heparosan, to a Drug for Enhanced Drug Delivery, Journal: Drug Development & Delivery, Year: 2013, pp. 1-4.
Chavaroche, A. et al. "Production Methods for Heparosan, a Precursor of Heparin and Heparan Sulfate." Carbohydrate Polymers. 2013 vol. 93 pp. 38-47.
Persson et al., "Variants of Recombinant Factor VIIa with Increased Intrinsic Activity," Seminars in Hematology , 2004, vol. 41, No. 1, Suppl 1, pp. 89-92.
Persson et al., "Augmented Intrinsic Activity of Factor VIIa by Replacement of Residues 305, 314, 337 and 374: Evidence of Two Unique Mutational Mechanisms of Activity Enhancement," Biochemical Journal, 2004, vol. 379, No., Pt. 2, pp. 497-503.
Persson et al., "Rational Design of Coagulation Factor VLLA Variants with Substantially Increased Intrinsic Activity," Proceedings of the National Academy of Sciences, 2001, vol. 98, No. 24, pp. 13583-13588.

* cited by examiner

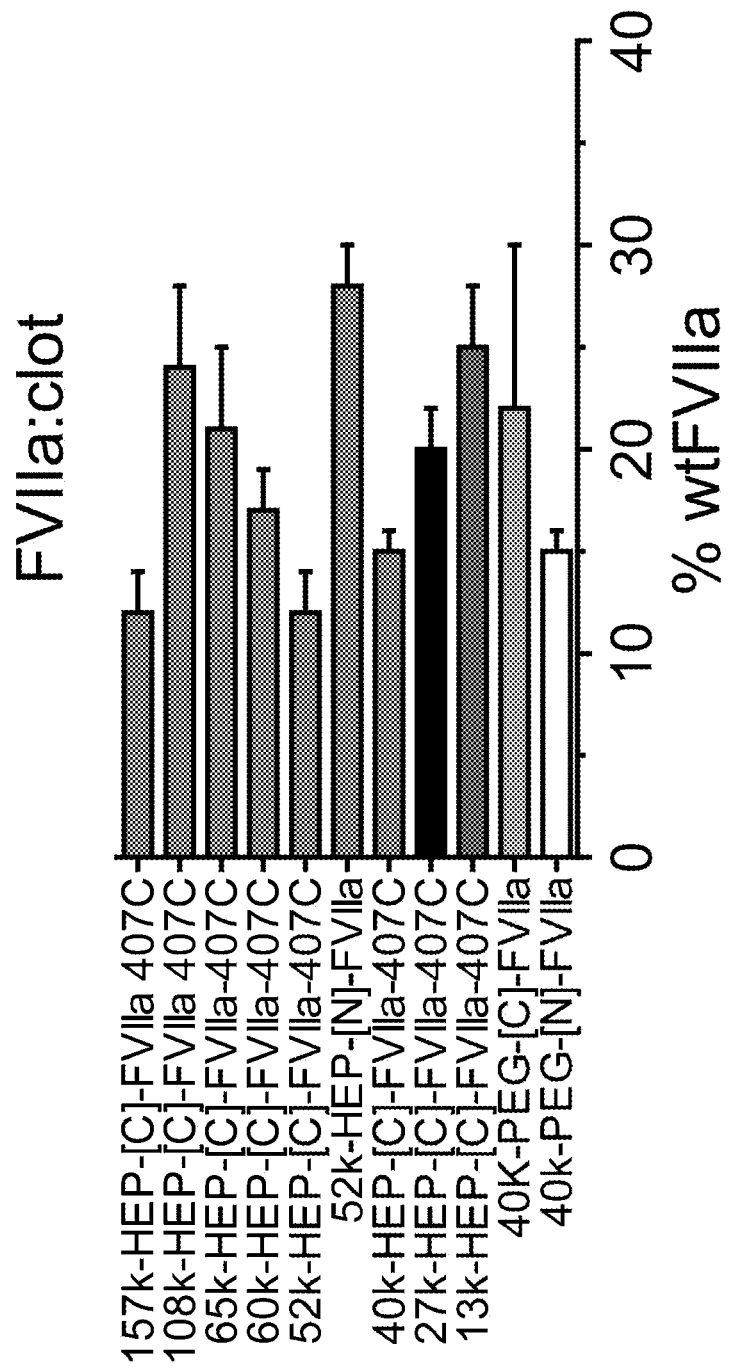

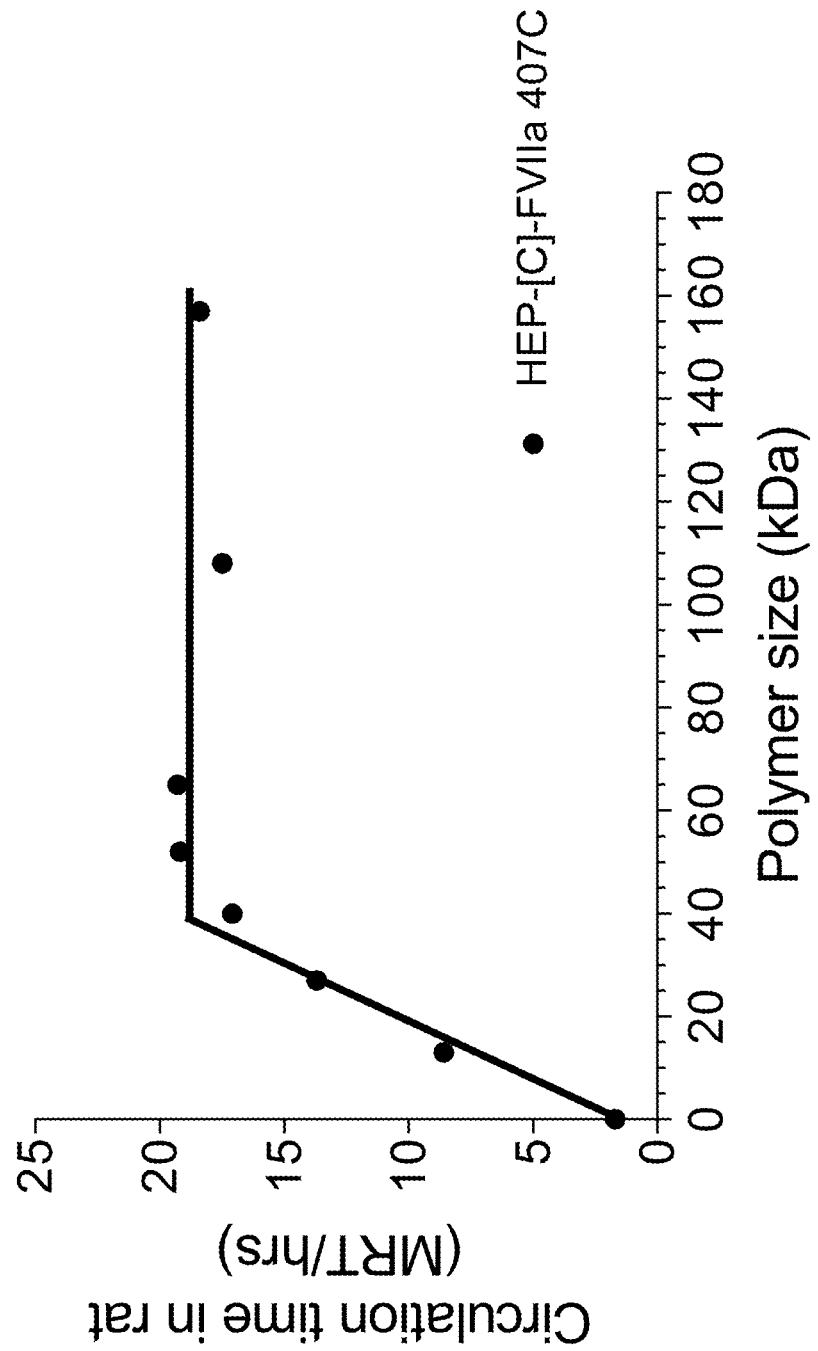

FACTOR VII CONJUGATES

CROSS-REFERENCE TO RELATED APPLICATIONS

This application is a continuation of U.S. application Ser. No. 14/433,151, filed Apr. 2, 2015, which is a 35 U.S.C. § 371 national stage application of International Patent Application PCT/EP2013/071499 (published as WO 2014/060397 A1), filed Oct. 15, 2013, which claimed priority of European Patent Application 12188472.0, filed Oct. 15, 2012; this application further claims priority under 35 U.S.C. § 119 of U.S. Provisional Application 61/715,929, filed Oct. 19, 2012; the contents of all above-named applications are incorporated herein by reference.

FIELD OF THE INVENTION

The present invention relates to the conjugation of Factor VII polypeptides with heparosan polymers.

BACKGROUND TO THE INVENTION

An injury to a blood vessel activates the haemostatic system that involves complex interactions between cellular and molecular components. The process that eventually causes the bleeding to stop is known as haemostasis. An important part of haemostasis is coagulation of the blood and the formation of a clot at the site of the injury. The coagulation process is highly dependent on the function of several protein molecules. These are known as coagulation factors. Some of the coagulation factors are proteases which can exist in an inactive zymogen or an enzymatically active form. The zymogen form can be converted to its enzymatically active form by specific cleavage of the polypeptide chain catalyzed by another proteolytically active coagulation factor. Factor VII is a vitamin K-dependent plasma protein synthesized in the liver and secreted into the blood as a single-chain glycoprotein. The Factor VII zymogen is converted into an activated form (Factor VIIa) by specific proteolytic cleavage at a single site, i.e. between R152 and I153 of the Factor VII sequence (wild type human coagulation Factor VII) resulting in a two chain molecule linked by a single disulfide bond. The two polypeptide chains in Factor VIIa are referred to as light and heavy chain, corresponding to residues 1-152 and 153-406, respectively, of the Factor VII sequence. Factor VII circulates predominantly as zymogen, but a minor fraction is on the activated form (Factor VIIa).

The blood coagulation process can be divided into three phases: initiation, amplification and propagation. The initiation and propagation phases contribute to the formation of thrombin, a coagulation factor with many important functions in haemostasis. The coagulation cascade starts if the single-layered barrier of endothelial cells that line the inner surface of blood vessels becomes damaged. This exposes subendothelial cells and extravascular matrix proteins to which platelets in the blood will stick to. If this happens, Tissue Factor (TF) which is present on the surface of sub-endothelial cells becomes exposed to Factor VIIa circulating in the blood. TF is a membrane-bound protein and serves as the receptor for Factor VIIa. Factor VIIa is an enzyme, a serine protease, with intrinsically low activity. However, when Factor VIIa is bound to TF, its activity increases greatly. Factor VIIa interaction with TF also localizes Factor VIIa on the phospholipid surface of the TF bearing cell and positions it optimally for activation of Factor X to Xa. When this happens, Factor Xa can combine with Factor Va to form the so-called "prothombinase" complex on the surface of the TF bearing cell. The prothrombinase complex then generates thrombin by cleavage of prothrombin. The pathway activated by exposing TF to circulating Factor VIIa and leading to the initial generation of thrombin is known as the TF pathway. The TF:Factor VIIa complex also catalyzes the activation of Factor IX to Factor IXa. Then activated Factor IXa can diffuse to the surface of platelets which are sticking to the site of the injury and have been activated. This allows Factor IXa to combine with FVIIIa to form the "tenase" complex on the surface of the activated platelet. This complex plays a key role in the propagation phase due to its remarkable efficiency in activating Factor X to Xa. The efficient tenase catalyzed generation of Factor Xa activity in turn leads to efficient cleavage of prothrombin to thrombin catalyzed by the prothrombinase complex.

If there are any deficiencies in either Factor IX or Factor VIII, it compromises the important tenase activity, and reduces the production of the thrombin which is necessary for coagulation. Thrombin formed initially by the TF pathway serves as a pro-coagulant signal that encourages recruitment, activation and aggregation of platelets at the injury site. This results in the formation of a loose primary plug of platelets. However, this primary plug of platelets is unstable and needs reinforcement to sustain haemostasis. Stabilization of the plug involves anchoring and entangling the platelets in a web of fibrin fibres.

The formation of a strong and stable clot is dependent on the generation of a robust burst of local thrombin activity. Thus, deficiencies in the processes leading to thrombin generation following a vessel injury can lead to bleeding disorders e.g. haemophilia A and B. People with haemophilia A and B lack functional Factor VIIIa or Factor IXa, respectively. Thrombin generation in the propagation phase is critically dependent of tenase activity, i.e. requires both Factor VIIIa and FIXa. Therefore, in people with haemophilia A or B proper consolidation of the primary platelet plug fails and bleeding continues.

Replacement therapy is the traditional treatment for hemophilia A and B, and involves intravenous administration of Factor VIII or Factor IX. In many cases, however, patients develop antibodies (also known as inhibitors) against the infused proteins, which reduce or negate the efficacy of the treatment. Recombinant Factor VIIa (Novoseven®) has been approved for the treatment of hemophilia A or B patients that have inhibitors, and also is used to stop bleeding episodes or prevent bleeding associated with trauma and/or surgery. Recombinant Factor VIIa also has been approved for the treatment of patients with congenital Factor VII deficiency. It has been proposed that recombinant FVIIa operates through a TF-independent mechanism. According to this model, recombinant FVIIa is directed to the surface of the activated blood platelets by virtue of its Gla-domain where it then proteolytically activates Factor X to Xa thus by-passing the need for a functional tenase complex. The low enzymatic activity of FVIIa in the absence of TF as well as the low affinity of the Gla-domain for membranes could explain the need for supra-physiological levels of circulating FVIIa needed to achieve haemostasis.

Recombinant Factor VIIa has a pharmacological half-life of 2-3 hours which may necessitate frequent administration to resolve bleedings in patients. Further, patients often only receive Factor VIIa therapy after a bleed has commenced, rather than as a precautionary measure, which often impinges upon their general quality of life. A recombinant Factor VIIa variant with a longer circulation half-life would decrease the number of necessary administrations and support less frequent dosing thus hold the promise of significantly improving Factor VIIa therapy to the benefit of patients and care-holders.

In general, there are many unmet medical needs in people with coagulopathies. The use of recombinant Factor VIIa to promote clot formation underlines its growing importance as a therapeutic agent. However, recombinant Factor VIIa therapy still leaves significant unmet medical needs, and there is a need for recombinant Factor VIIa polypeptides having improved pharmaceutical properties, for example increased in vivo functional half-life, improved activity, and less undesirable side effects.

Various methods have been employed in the development of a Factor VII polypeptide with prolonged circulatory half-life. Some of these methods relate to conjugation of Factor VII with water soluble polymers such as PEG (poly ethylene glycol). WO03031464 disclose an enzymatic approach where PEG groups can be attached to glycans present on the polypeptide.

SUMMARY OF THE INVENTION

The present invention derives from the finding that the polymer heparosan can be bound to Factor VII in order to extend its half-life. One advantage with heparosan is that heparosan polymers are biodegradable, avoiding any potential accumulation problems related to non-biodegradable polymers. The use of heparosan polymers in this way can lead to improved properties of Factor VII polypeptide conjugates such as increased FIXa and FXa generation potential and improved clot activity.

Accordingly, the present invention provides a conjugate between a Factor VII polypeptide and a heparosan polymer.

In interesting embodiments, the polymer may have a polydispersity index (Mw/Mn) of less than 1.10 or less than 1.05. In another interesting embodiment, the polymer may have a size between 13 kDa and 65 kDa.

The heparosan Factor VII polypeptide conjugate of the invention may have increased circulating half-life compared to an un-conjugated Factor VII polypeptide; or increased functional half-life compared to an un-conjugated Factor VII polypeptide.

The heparosan Factor VII polypeptide conjugate of the invention may have increased mean residence time compared to an un-conjugated Factor VII polypeptide; or increased functional mean residence time compared to an un-conjugated Factor VII polypeptide.

The Factor VII polypeptide may be a variant of a Factor VII polypeptide carrying a free cysteine, such as FVIIa-407C, in which the heparosan polymer may be attached to the cysteine at position 407 of said Factor VII polypeptide. The polymer may be attached to the polypeptide via N- or O-glycans.

The invention also provides compositions comprising the conjugates described herein, such as a pharmaceutical composition comprising a conjugate of the invention and a pharmaceutically acceptable carrier or diluent.

A conjugate or composition of the invention may be provided for use in a method of treating or preventing a bleeding disorder. That is, the invention relates to methods of treating or preventing a bleeding disorder, wherein said methods comprise administering a suitable dose of a conjugate of the invention to a patient in need thereof, such as an individual in need of Factor VII, such as an individual having haemophilia A or haemophilia B.

BRIEF DESCRIPTION OF THE FIGURES

FIG. 3: Analysis of FVIIa clotting activity levels of heparosan conjugates and glycoPEGylated FVIIa references.

FIG. 7: Relationship between HEP-size and mean residence time (MRT) for a number of HEP-[C]-FVIIa407C conjugates. MRT values from PK studies are plotted against heparosan polymer size of conjugates. The plot represent values for non-conjugated FVIIa, 13k-HEP-[C]-FVIIa407C, 27k-HEP-[C]-FVIIa407C, 40k-HEP-[C]-FVIIa407C, 52k-HEP-[C]-FVIIa407C, 65k-HEP-[C]-FVIIa407C, 108k-HEP-[C]-FVIIa407C and 157k-HEP-[C]-FVIIa407C. MRT (LOCI) was calculated by non-compartmental methods using Phoenix WinNonlin 6.0 (Pharsight Corporation).

DETAILED DESCRIPTION OF THE INVENTION

Figure 1A:
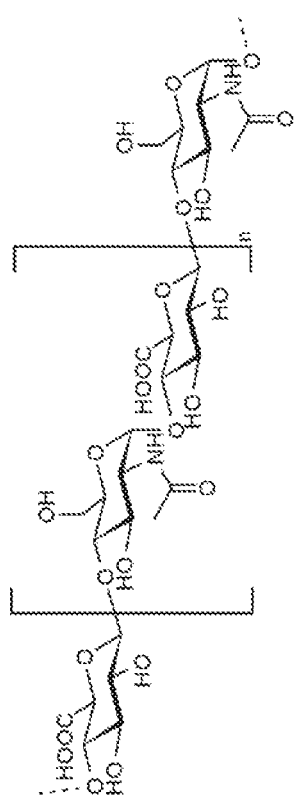
FIG. 1A shows the structure of heparosan.

The invention relates to conjugates between Factor VII (FVII) polypeptides and heparosan (HEP) polymers, as well as to methods for preparing such conjugates and uses for such conjugates. The Inventors have surprisingly found that Factor VII-heparosan conjugates have improved properties.

Factor VII Polypeptides.

The terms "Factor VII" or "FVII" denote Factor VII polypeptides. Suitable polypeptides may be produced by methods including natural source extraction and purification, and by recombinant cell culture systems. The sequence and characteristics of wild-type human Factor VII are set forth, for example, in U.S. Pat. No. 4,784,950.

Also encompassed within the term "Factor VII polypeptide" are biologically active factor VII equivalents and modified forms of Factor VII, e.g., differing in one or more amino acid(s) in the overall sequence. Furthermore, the terms used in this application are intended to cover substitution, deletion and insertion amino acid variants of Factor VII or posttranslational modifications.

As used herein, "Factor VII polypeptide" encompasses, without limitation, Factor VII, as well as Factor VII-related polypeptides. Factor VII-related polypeptides include, without limitation, Factor VII polypeptides that have either been chemically modified relative to human Factor VII and/or contain one or more amino acid sequence alterations relative to human Factor VII (i.e., Factor VII variants), and/or contain truncated amino acid sequences relative to human Factor VII (i.e., Factor VII fragments). Such factor VII-related polypeptides may exhibit different properties relative to human Factor VII, including stability, phospholipid binding, altered specific activity, and the like.

The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

The term "Factor VII" is also intended to encompass, without limitation, polypeptides having the amino acid sequence 1-406 of wild-type human Factor VII (as disclosed in U.S. Pat. No. 4,784,950), as well as wild-type Factor VII derived from other species, such as, e.g., bovine, porcine, canine, murine, and salmon Factor VII. It further encompasses natural allelic variations of Factor VII that may exist and occur from one individual to another. Also, degree and location of glycosylation or other post-translation modifications may vary depending on the chosen host cells and the nature of the host cellular environment.

As used herein, "Factor VII-related polypeptides" encompasses, without limitation, polypeptides exhibiting substantially the same or improved biological activity relative to wild-type human Factor VII. These polypeptides include, without limitation, Factor VII or Factor VIIa that has been chemically modified and Factor VII variants into which specific amino acid sequence alterations have been introduced that modify or disrupt the bioactivity of the polypeptide.

Also encompassed are polypeptides with a modified amino acid sequence, for instance, polypeptides having a modified N-terminal end including N-terminal amino acid deletions or additions, and/or polypeptides that have been chemically modified relative to human Factor VIIa.

Also encompassed are polypeptanides with a modified amino acid sequence, for instance, polypeptides having a modified C-terminal end including C-terminal amino acid deletions or additions, and/or polypeptides that have been chemically modified relative to human Factor VIIa.

Factor VII-related polypeptides, including variants of Factor VII, exhibiting substantially the same or better bioactivity than wild-type Factor VII, include, without limitation, polypeptides having an amino acid sequence that differs from the sequence of wild-type Factor VII by insertion, deletion, or substitution of one or more amino acids.

Factor VII-related polypeptides, including variants, having substantially the same or improved biological activity relative to wild-type Factor VIIa encompass those that exhibit at least about 25%, preferably at least about 50%, more preferably at least about 75%, more preferably at least about 100%, more preferably at least about 110%, more preferably at least about 120%, and most preferably at least about 130% of the specific activity of wild-type Factor VIIa that has been produced in the same cell type, when tested in one or more of a clotting assay, proteolysis assay, or TF binding assay.

The Factor VII polypeptide may be a Factor VII-related polypeptide, in particular a variant, wherein the ratio between the activity of said Factor VII polypeptide and the activity of native human Factor VIIa (wild-type FVIIa) is at least about 1.25 when tested in an in vitro hydrolysis assay; in other embodiments, the ratio is at least about 2.0; in further embodiments, the ratio is at least about 4.0. The Factor VII polypeptide may be a Factor VII analogue, in particular a variant, wherein the ratio between the activity of said Factor VII polypeptide and the activity of native human Factor VIIa (wild-type FVIIa) is at least about 1.25 when tested in an in vitro proteolysis assay; the ratio may be at least about 2.0; the ratio may be at least about 4.0; the ratio may be at least about 8.0.

The Factor VII polypeptide may be human Factor VII, as disclosed, e.g., in U.S. Pat. No. 4,784,950 (wild-type Factor VII). The Factor VII polypeptide may be human Factor VIIa. Factor VII polypeptides include polypeptides that exhibit at least about 90%, preferably at least about 100%, preferably at least about 120%/o, more preferably at least about 140%, and most preferably at least about 160%, of the specific biological activity of human Factor VIIa.

The Factor VII polypeptide may be a variant Factor VII polypeptide having a reduced interaction with antithrombin III when compared to that of human Factor VIIa. For example, the Factor VII polypeptide may have less than 100%, less than 95%, less than 90%, less than 80%, less than 70% or less than 50%/c of the interaction with antithrombin III of wild type human Factor VIIa. A reduced interaction with antithrombin III may be present in combination with another improved biological activity as described herein, such as an improved proteolytic activity.

The Factor VII polypeptide may have an amino acid sequence that differs from the sequence of wild-type Factor VII by insertion, deletion, or substitution of one or more amino acids.

The Factor VII polypeptide may be a polypeptide that exhibits at least about 70%, preferably at least about 80%, more preferably at least about 90%, and most preferable at least about 95%, of amino acid sequence identity with the sequence of wild-type Factor VII as disclosed in U.S. Pat. No. 4,784,950. Amino acid sequence homology/identity is conveniently determined from aligned sequences, using a suitable computer program for sequence alignment, such as, e.g., the ClustalW program, version 1.8, 1999 (Thompson et al., 1994, Nucleic Acid Research, 22: 4673-4680).

Non-limiting examples of Factor VII variants having substantially the same or improved biological activity as wild-type Factor VII include S52A-FVII, S60A-FVII (lino et al., Arch. Biochem. Biophys. 352: 182-192, 1998); L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII; FVIIa variants exhibiting increased TF-independent activity as disclosed in WO 01/83725 and WO 02/22776; FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); and oxidized forms of Factor VIIa (Kornfelt et al., Arch. Biochem. Biophys. 363:43-54, 1999).

Further Factor VII variants falling within the scope of Factor VII polypeptides herein are those described in WO 2007/031559 and WO 2009/126307.

Preferred Factor VII polypeptides for use in accordance with the present invention are those in which an additional cysteine residue has been added compared to an existing FVII sequence, such as a wild type FVII sequence. The cysteine may be appended to a Factor VII polypeptide at the C-terminal. The cysteine may be appended to a Factor VIIa polypeptide at the C-terminal residue 406 of the amino acid sequence of wild-type human Factor VII, leading to FVIIa 407C. The cysteine may be positioned in the amino acid sequence of a Factor VII molecule at a surface exposed position that will not seriously impede tissue factor binding, Factor X binding or binding to phospholipids. The structure of Factor VIIa is known and a suitable position meeting these requirements may therefore be identified by the skilled person.

The numbering of amino acids in the Factor VII polypeptide set out herein is based on the amino acid sequence for wild type human Factor VII as disclosed in U.S. Pat. No. 4,784,950. It will be apparent that equivalent positions in other Factor VII polypeptides may be readily identified by the skilled person by carrying out an alignment of the relevant sequences.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively).

The biological activity of a Factor VII polypeptide may be measured by a number of ways as described below:

Peptidolytic Activity Using Chromogenic Substrate (S-2288)

The peptidolytic activity of a FVII polypeptide or a FVII conjugate can be estimated using a chromogenic peptide (S-2288; Chromogenix) as substrate. A way of performing the assay is as follows: FVII polypeptide and appropriate FVIIa reference proteins are diluted in 50 mM HEPES, 5 mM CaCl2, 100 mM NaCl, 0.01% Tween80, pH 7.4. The kinetic parameters for cleavage of the chromogenic substrate S-2288 are then determined in 96-well plate (n=3). In a typical experiment, 135 ul HEPES buffer, 10 ul of 200 nM FVIIa test entity solutions and 50 ul of 200 nM tissue factor stock solutions is added to the well. The micro plate is left for 5 minutes. The reaction is then initiated by addition of 10 ul of 10 mM S-2288 stock solution. The absorbance increase is measured continuously at 405 nm in a SpectraMax 190 microplate reader for 15 min. at room temperature. The amount of substrate converted is determined on the basis of a pNA (para-nitroaniline) standard curve. Relative activities are calculated from the initial rates, and compared to FVIIa rates. Activities for FVIIa conjugates can then be reported as a percentage of the activity of FVIIa reference.

Proteolytic Activity Using Plasma-Derived Factor X as Substrate

The proteolytic activity of a FVII polypeptide or a FVII conjugate can be estimated using plasma-derived factor X (FX) as substrate. A way of performing the assay is as follows: All proteins are initially diluted in 50 mM HEPES (pH 7.4), 100 mM NaCl, 10 mM $CaCl_2$, 1 mg/mL BSA, and 0.1% (w/v) PEG8000. The kinetic parameters for FX activation are then determined by incubating 10 nM of each FVII polypeptide or conjugate with 40 nM FX in the presence of 25 uM PC:PS phospholipids (Haematologic technologies) for 30 min at room temperature in a total reaction volume of 100 uL in a 96-well plate (n=2). FX activation in the presence of soluble tissue factor (sTF) is determined by incubating 5 pM of each FVII polypeptide or FVII conjugate with 30 nM FX in the presence of 25 uM PC:PS phospholipids for 20 min at room temperature in a total reaction volume of 100 uL (n=2). After incubation, reactions are quenched by adding 50 uL stop buffer [50 mM HEPES (pH 7.4), 100 mM NaCl, 80 mM EDTA] followed by the addition of 50 uL 2 mM chromogenic peptide S-2765 (Chromogenix). Finally, the absorbance increase is measured continuously at 405 nm in a Spectramax 190 microplate reader. Catalytic efficiencies ($k_{cat}/K_m$) is determined by fitting the data to a revised form of the Michaelis Menten equation ([S]<Km) using linear regression. The amount of FXa generated is estimated from a FXa standard curve.

Assay for Measuring Clotting Time:

For the purposes of the invention, biological activity of Factor VII polypeptides ("Factor VII biological activity") or of conjugates of the invention may also be quantified by measuring the ability of a preparation to promote blood clotting using Factor VII-deficient plasma and thromboplastin, as described, e.g., in U.S. Pat. No. 5,997,864 or WO 92/15686. In this assay, biological activity is expressed as the reduction in clotting time relative to a control sample and is converted to "Factor VII units" by comparison with a pooled human serum standard containing 1 unit/ml Factor VII activity.

Assay for Determining Binding to Tissue Factor:

Alternatively, Factor VIIa biological activity may be quantified by measuring the physical binding of Factor VIIa or a Factor VII-related polypeptide to TF using an instrument based on surface plasmon resonance (Persson, FEBS Letts. 413:359-363, 1997).

Potency as Measured by Soluble TF Dependent Plasma-Based FVIIa Clot Assay

Potencies can be estimated using a commercial FVIIa specific clotting assay; STACLOT®VIIa-rTF from Diagnostica Stago. The assay is based on the method published by J. H. Morrissey et al, Blood. 81:734-744 (1993). It measures sTF initiated FVIIa activity-dependent time to fibrin clot formation in FVII deficient plasma in the presence of phospholipids. Test compounds are diluted in Pipes+1% BSA assay dilution buffer and tested in 4 dilutions in 4 separate assay runs. Clotting times can be measured on an ACL9000 (ILS) coagulation instrument and results calculated using linear regression on a bilogarithmic scale based on a FVIIa calibration curve.

Pharmacokinetic Evaluation in Sprauge Dawley Rats

The pharmacokinetic properties of a FVII polypeptide or a FVII conjugate can be estimated in sprauge Dawley rats. One way of performing such an animal study is as follows: The FVII polypeptide or FVII conjugate is initially formulated in a suitable buffer such as 10 mM Histidine, 100 mM NaCl, 10 mM $CaCl_2$, 0.01% Tween80 80, pH 6.0 and FVII polypeptide or FVII conjugate concentration in formulation buffer is determined by light chain quantification on HPLC. Male Sprague Dawley rats are obtained for the study. The animals are allowed at least one week acclimatisation period, and are allowed free access to feed and water before start of the experiment. The FVII polypeptide or FVII conjugate formulations are then given as a single iv bolus injection in the tail vein. Blood is then samples according to a predetermined schedule. Blood can be sampled the following way: 45 µl of blood is transferred to an Eppendorf tube containing 5 µl Stabilyte; 200 µl PIPES buffer (0.050 M Pipes, 0.10 M sodium chloride, 0.002 M EDTA, 1% (w/v) BSA, pH 7.2.) is added and inverted gently 5 times. The diluted citrate-stabilised blood is kept at room temperature until centrifugation at 4000 G for 10 minutes at room temperature. After centrifugation the supernatant is divided to three Micronic tubes; 70 ul for clot activity, 70 ul for antigen analysis and the rest as extra sample. The samples are immediately frozen on dry ice and storage at −80° C. until plasma analysis for example as described below can be carried out.

Plasma Analysis; FVIIa-Clot Activity Level

FVIIa clotting activity levels of FVII polypeptide or a FVII conjugate in rat plasma can be estimated using a commercial FVIIa specific clotting assay; such as STACLOT®VIIa-rTF from Diagnostica Stago. The assay is based on the method published by J. H. Morrissey et al, Blood. 81:734-744 (1993). It measures soluble tissue factor (sTF) initiated FVIIa activity-dependent time to fibrin clot formation in FVII deficient plasma in the presence of phospholipids. Samples can be measured on an ACL9000 coagulation instrument against FVIIa calibration curves with the same matrix as the diluted samples (like versus like).

Plasma Analysis; Antigen Concentration

FVII polypeptide or FVII conjugate antigen concentrations in plasma can be determined using LOCI technology. In this method, two monoclonal antibodies against human FVII are used for detection. The principle is described in Thromb Haemost 100(5):920-8 (2008). Samples are measured against drug substance calibration curves.

Pharmacokinetic Analysis

Pharmacokinetic analysis can be carried out by non-compartmental methods (NCA) using for example WinNonlin (Pharsight Corporation St. Louis, Mo.) software. From the data the following parameters can be estimated: $C_{max}$ (maximum concentration), $T_{max}$ (time of maximum concentration), AUC (area under the curve from zero to infinity), $AUC_{extrap}$ (percentage of AUC that are extrapolated from the last concentration to infinity), $T_{1/2}$ (half-life), Cl (clearance) Vz (volume of distribution), and MRT (mean residence time).

These methods set out a comparison between a Factor VII polypeptide and wild-type Factor VIIa. However, it will be apparent that the same methods can also be used to compare the activity of a Factor VII polypeptide of interest with any other Factor VII polypeptide. For example, such a method may be used to compare the activity of a conjugate as described herein with a suitable control molecule such as an unconjugated Factor VII polypeptide, a Factor VII polypeptide that is conjugated with a water soluble polymer other than heparosan or a Factor VII polypeptide that is conjugated to a PEG, such as a 40 kDa PEG, rather than conjugated to heparosan. A method described herein, such as an in vitro hydrolysis assay or an in vitro proteolysis assay can therefore be adapted by substituting the Factor VIIa wild type polypeptide in the above methods with the control molecule of interest.

The ability of factor VIIa or Factor VII polypeptides to generate thrombin can also be measured in an assay comprising all relevant coagulation factors and inhibitors at physiological concentrations (minus factor VIII when mimicking hemophilia A conditions) and activated platelets (as described on p. 543 in Monroe et al. (1997) Brit. J. Haematol. 99, 542-547, which is hereby incorporated as reference)

The activity of the Factor VII polypeptides may also be measured using a one-stage clot assay (assay 4) essentially as described in WO 92/15686 or U.S. Pat. No. 5,997,864. Briefly, the sample to be tested is diluted in 50 mM Tris (pH 7.5), 0.1% BSA and 100 µl is incubated with 100 µl of Factor VII deficient plasma and 200 µl of thromboplastin C containing 10 mM $Ca^{2+}$. Clotting times are measured and compared to a standard curve using a reference standard or a pool of citrated normal human plasma in serial dilution.

Human purified Factor VIIa suitable for use in the present invention may be made by DNA recombinant technology, e.g. as described by Hagen et al., Proc. Natl. Acad. Sci. USA 83: 2412-2416, 1986, or as described in European Patent No. 200.421 (ZymoGenetics, Inc.). Factor VII may also be produced by the methods described by Broze and Majerus, J. Biol. Chem. 255 (4): 1242-1247, 1980 and Hedner and Kisiel, J. Clin. Invest. 71: 1836-1841, 1983. These methods yield Factor VII without detectable amounts of other blood coagulation factors. An even further purified Factor VII preparation may be obtained by including an additional gel filtration as the final purification step. Factor VII is then converted into activated factor VIIa by known means, e.g. by several different plasma proteins, such as factor XIIa, IX a or Xa Alternatively, as described by Bjoern et al. (Research Disclosure, 269 September 1986, pp. 564-565), factor VII may be activated by passing it through an ion-exchange chromatography column, such as Mono Q® (Pharmacia fine Chemicals) or the like, or by autoactivation in solution.

Factor VII-related polypeptides may be produced by modification of wild-type Factor VII or by recombinant technology. Factor VII-related polypeptides with altered amino acid sequence when compared to wild-type Factor VII may be produced by modifying the nucleic acid sequence encoding wild-type factor VII either by altering the amino acid codons or by removal of some of the amino acid codons in the nucleic acid encoding the natural factor VII by known means, e.g. by site-specific mutagenesis.

The introduction of a mutation into the nucleic acid sequence to exchange one nucleotide for another nucleotide may be accomplished by site-directed mutagenesis using any of the methods known in the art. Particularly useful is the procedure that utilizes a super coiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl, which is specific for methylated and hemimethylated DNA to digest the parental DNA template and to select for mutation-containing synthesized DNA. Other procedures known in the art for creating, identifying and isolating variants may also be used, such as, for example, gene shuffling or phage display techniques.

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, Factor VII polypeptides may be further purified. Purification may be achieved using any method known in the art, including, without limitation, affinity chromatography, such as, e.g., on an anti-Factor VII antibody column (see, e.g., Wakabayashi et al., J. Biol. Chem. 261:11097, 1986; and Thim et al., Biochem. 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J. C. Janson and Lars Ryden, editors, VCH Publishers, New York, 1989. Following purification, the preparation preferably contains less than about 10% by weight, more preferably less than about 5% and most preferably less than about 1%, of non-Factor VII polypeptides derived from the host cell.

Factor VII polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., Biochem. 11:2853 (1972); Thomas, U.S. Pat. No. 4,456,591; and Hedner et al., J. Clin. Invest. 71:1836 (1983). Alternatively, Factor VII polypeptides may be activated by passing it through an ion-exchange chromatography column, such as Mono Q® (Pharmacia) or the like, or by autoactivation in solution. The resulting activated Factor VII polypeptide may then be conjugated with a heparosan polymer, formulated and administered as described in the present application.

Heparosan Polymers

Heparosan (HEP) is a natural sugar polymer comprising (-GlcUA-beta1,4-GlcNAc-alpha1,4-) repeats (see FIG. 1A). It belongs to the glycosaminoglycan polysaccharide family and is a negatively charged polymer at physiological pH. It can be found in the capsule of certain bacteria but it is also found in higher vertebrate where it serves as precursor for the natural polymers heparin and heparan sulphate. Although not proven in detail, heparosan is believed to be degraded in the lysosomes. An injection of a 100 kDa heparosan polymer labelled with Bolton-Hunter reagents has shown that heparosan is secreted as smaller fragments in body fluids/waste (US 2010/0036001).

Heparosan polymers and methods of making such polymers are described in US 2010/0036001, the content of which is incorporated herein by reference. In accordance with the present invention, the heparosan polymer may be any heparosan polymer described or disclosed in US 2010/0036001.

For use in the present invention, heparosan polymers can be produced by any suitable method, such as any of the methods described in US 2010/0036001 or US 2008/0109236. Heparosan can be produced using bacterial-derived enzymes. For example, the heparosan synthase PmHS1 of *Pasteurella mutocida* Type D polymerises the heparosan sugar chain by transferring both GlcUA and GlcNAc. The *Escherichia coli* K5 enzymes KfiA (alpha GlcNAc transferase) and KfiC (beta GlcUA transferase) can together also form the disaccharide repeat of heparosan.

A heparosan polymer for use in the present invention is typically a polymer of the formula (-GlcUA-beta1,4-GlcNAc-alpha1,4-)n.

The size of the heparosan polymer may be defined by the number of repeats n in this formula. The number of said repeats n may be, for example, from 2 to about 5000. The number of repeats may be, for example 50 to 2000 units, 100 to 1000 units or 200 to 700 units. The number of repeats may be 200 to 250 units, 500 to 550 units or 350 to 400 units. Any of the lower limits of these ranges may be combined with any higher upper limit of these ranges to form a suitable range of numbers of units in the heparosan polymer.

The size of the heparosan polymer may be defined by its molecular weight. The molecular weight may be the average molecular weight for a population of heparosan polymer molecules, such as the weight average molecular mass.

Molecular weight values as described herein in relation to size of the heparosan polymer may not, in practise, exactly be the size listed. Due to batch to batch variation during heparosan polymer production, some variation is to be expected. To encompass batch to batch variation, it is therefore to be understood, that a variation around +/−5%, 4%, 3%, 2% or 1% around target heparosan polymer size could be expected. For example heparosan polymer size of 40 kDa denotes 40 kD+/−5%, e.g. 40 kDa could for example in practise mean 38.8 kDa or 41.5 kDa.

The heparosan polymer may have a molecular weight of, for example, 500 Da to 1,000 kDa. The molecular weight of the polymer may be 500 Da to 650 kDa, 5 kDa to 750 kDa, 10 kDa to 500 kDa, 15 kDa to 550 kDa or 25 kDa to 250 kDa.

The molecular weight may be selected at particular levels within these ranges in order to achieve a suitable balance between activity of the Factor VII polypeptide and half-life or mean residence time of the conjugate. For example, the molecular weight of the polymer may be in a range selected from 15-25 kDa, 25-35 kDa, 35-45 kDa, 45-55 kDa, 55-65 kDa or 65-75 kDa.

More specific ranges of molecular weight may be selected. For example, the molecular weight may be 20 kDa to 35 kDa, such as 22 kDa to 32 kDa such as 25 kDa to 30 kDa, such as about 27 kDa. The molecular weight may be 35 to 65 kDa, such as 40 kDa to 60 kDa, such as 47 kDa to 57 kDa, such as 50 kDa to 55 kDa such as about 52 kDa. The molecular weight may be 50 to 75 kDa such as 60 to 70 kDa, such as 63 to 67 kDa such as about 65 kDa.

In particularly interesting embodiments, the heparosan polymer of the Factor VII conjugate, of the invention, has a size in a range selected from 13-65 kDa, 13-55 kDa, 25-55 kDa, 25-50 kDa, 25-45 kDa, 30-45 kDa and 38-42 kDa.

Any of the lower limits of these ranges of molecular weight may be combined with any higher upper limit from these ranges to forma a suitable range for the molecular weight of the heparosan polymer in accordance with the invention.

The heparosan polymer may have a narrow size distribution (i.e. monodisperse) or a broad size distribution (i.e. polydisperse). The level of polydispersity (PDI) may be represented numerically based on the formula Mw/Mn, where Mw=weight average molecular mass and Mn=number average molecular weight. The polydispersity value using this equation for an ideal monodisperse polymer is 1. Preferably, a heparosan polymer for use in the present invention is monodisperse. The polymer may therefore have a polydispersity that is about 1, the polydispersity may be less than 1.25, preferably less than 1.20, preferably less than 1.15, preferably less than 1.10, preferably less than 1.09, preferably less than 1.08, preferably less than 1.07, preferably less than 1.06, preferably less than 1.05.

The molecular weight size distribution of the heparosan may be measured by comparison with monodisperse size standards (HA Lo-Ladder, Hyalose LLC) which may be run on agarose gels.

Alternatively, the size distribution of heparosan polymers may be determined by high performance size exclusion chromatography-multi angle laser light scattering (SEC- MALLS). Such a method can be used to assess the molecular weight and polydispersity of a heparosan polymer.

Figure 1B:
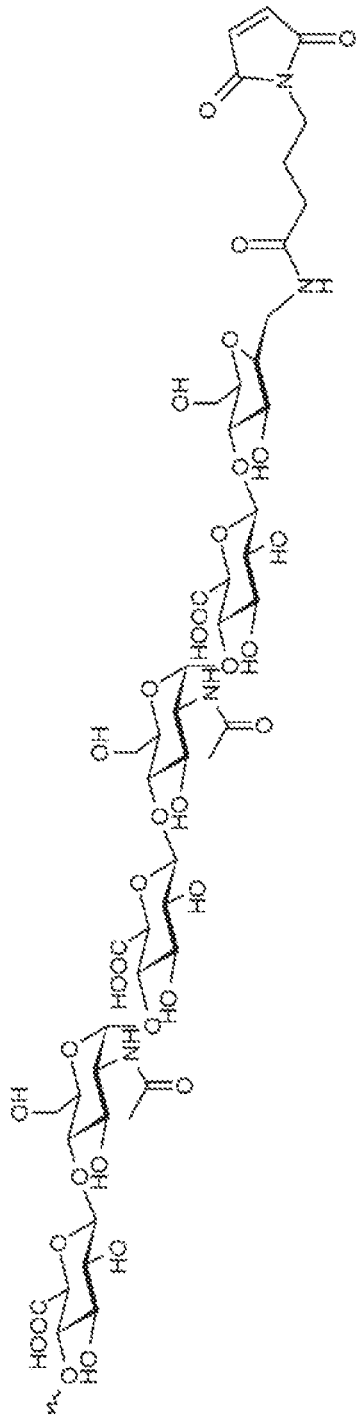
FIG. 1B shows the structure of a heparosan polymer with maleimide functionality at its reducing end.
Figure 2B:
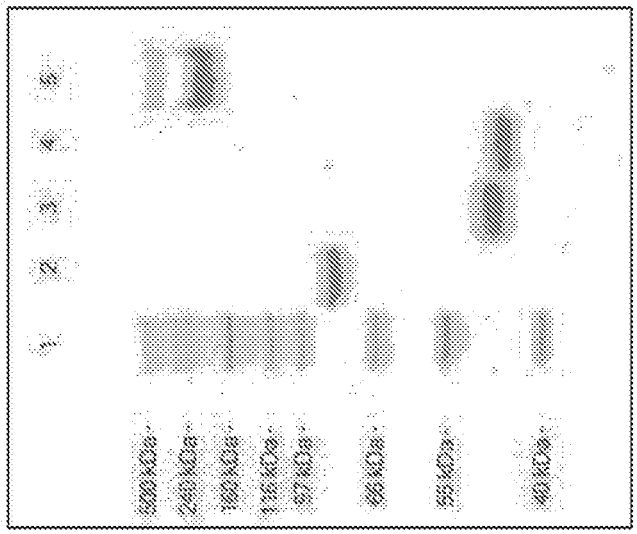
FIG. 2B shows a SDS-PAGE of glycoconjugated 52k-HEP-[N]-FVIIa. Gel was loaded with HiMark HMW standard (lane 1), ST3Gal3 (lane 2), FVIIa (lane 3), asialo FVIIa (lane 4), and 52k-HEP-[N]-FVIIa (lane 5).
Figure 2A:
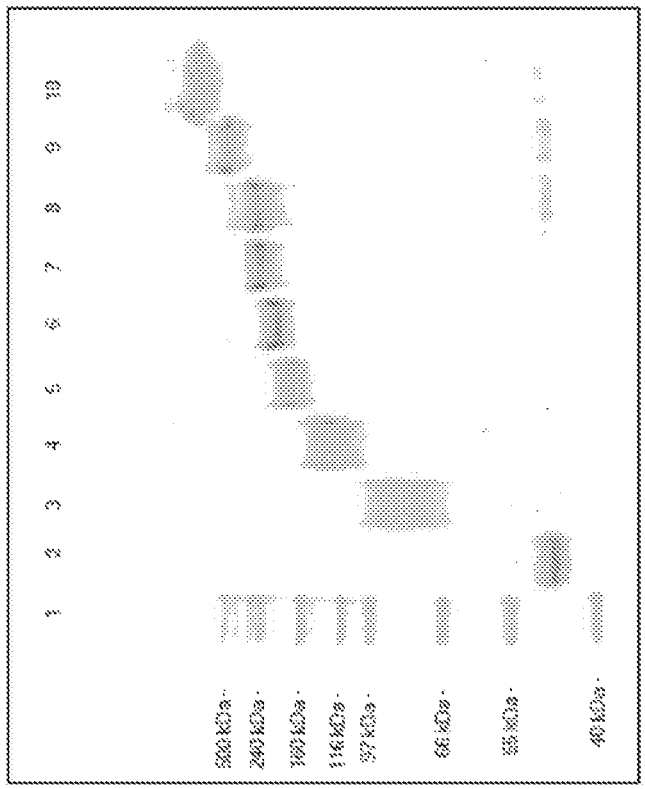
FIG. 2A shows a SDS-PAGE analysis of final FVIIa conjugates. Gel was loaded with HiMark HMW standard (lane 1); FVIIa (lane 2); 13k-HEP-[C]-FVIIa (lane 3); 27k-HEP-[C]-FVIIa (lane 4); 40k-HEP-[C]-FVIIa (lane 5); 52k-HEP-[C]-FVIIa (lane 6); 60k-HEP-[C]-FVIIa (lane 7); 65k-HEP-[C]-FVIIa (lane 8); 108k-HEP-[C]-FVIIa (lane 9) and 157k-HEP-[C]-FVIIa407C (lane 10).

Polymer size may be regulated in enzymatic methods of production. By controlling the molar ratio of heparosan acceptor chains to UDP sugar, it is possible to select a final heparosan polymer size that is desired The heparosan polymer may further comprise a reactive group to allow its attachment to a Factor VII polypeptide. A suitable reactive group may be, for example, an aldehyde, alkyne, ketone, maleimide, thiol, azide, amino, hydrazide, hydroxylamine, carbonate, ester, chelator or a combination of any thereof. For example, FIG. 1B illustrates a heparosan polymer comprising a maleimide group.

Further examples of reactive groups that can be added to the heparosan polymer are as follows:
- aldehyde reaction group added at the reducing terminus, reactive with amines
- maleimide group added at the reducing terminus, reactive with sulfhydryls
- pyridylthio group added at the reducing terminus, reactive with sulfhydryls
- azido group added at the non-reducing terminus or within the sugar chain, reactive with acetylenes
- amino group added at the reducing terminus, non-reducing terminus or within the sugar chain, reactive with aldehydes
- N-hydroxy succinimide group added at the reducing or non-reducing terminus, reactive with amines
- Hydroxylamine group added at the reducing or non-reducing terminus, react with aldehydes and ketones.
  - hydrazide added at the reducing terminus, reactive with aldehydres or ketones.

As set out in the Examples, maleimide functionalized heparosan polymers of defined size may be prepared by an enzymatic (PmHS1) polymerization reaction using the two sugar nucleotides UDP-GlcNAc and UDP-GlcUA in equimolar amount. A priming trisaccharide (GlcUA-GlcNAc-GlcUA)NH$_2$ may be used for initiating the reaction, and polymerization run until depletion of sugar nucleotide building blocks. Terminal amine (originating from the primer) may then be functionalized with suitable reactive groups such as a reactive group as described above, such as a maleimide functionality designed for conjugation to free cysteines. The size of the heparosan polymers can be pre-determined by variation in sugar nucleotide: primer stoichiometry. The technique is described in detail in US 2010/0036001.

The reactive group may be present at the reducing or non-reducing termini or throughout the sugar chain. The presence of only one such reactive group is preferred when conjugating the heparosan polymer to the polypeptide.

Methods for Preparing FVII-HEP Conjugates

According to the present invention, a Factor VII polypeptide as described herein is conjugated to a heparosan polymer as described herein. Any Factor VII polypeptide as described herein may be combined with any heparosan polymer as described herein.

The heparosan polymer may be attached at a single position on the polypeptide, or heparosan polymers may be attached at multiple positions on the polypeptide.

The location of attachment of the polymer to the polypeptide may depend on the particular polypeptide molecule being used. The location of attachment of the polymer to the polypeptide may depend on the type of reactive group, if any, that is present on the polymer. As explained above, different reactive groups will react with different groups on the polypeptide molecule.

Various methods of attaching polymers to polypeptides exist and any suitable method may be used in accordance with the present invention. Heparosan polymers may be attached to the glycans of a Factor VII polypeptide using attachment technology described in any of US 2010/0036001, WO03/031464, WO2005/014035 or WO2008/025856, the content of each of which is included herein by reference.

For example, WO 03/031464 describes methods for remodelling the glycan structure of a polypeptide, such as a Factor VII or Factor VIIa polypeptide and methods for the addition of a modifying group such as a water soluble polymer to such a polypeptide. Such methods may be used to attach a heparosan polymer to a Factor VII polypeptide in accordance with the present invention.

As set out in the Examples, a Factor VII polypeptide may be conjugated to its glycan moieties using sialyltransferase. For enablement of this approach, a HEP polymer first need to be linked to a sialic acid cytidine monophosphate. 5'-glycylamidoneuraminic acid cytidine monophosphate (GSC) is a suitable starting point for such chemistry, but other sialic acid cytidine monophosphate or fragments of such can be used. Examples set out methods for covalent linking HEP polymers to GSC molecules. By covalent attachment, a HEP-GSC (HEP conjugated glycylamidoneuraminic acid cytidine monophosphate) molecule is created that can be transferred to glycan moieties of FVIIa.

WO 2005/014035 describes chemical conjugation that utilises galactose oxidase in combination with terminal galactose-containing glycoproteins such as sialidase treated glycoproteins or asialo glycoproteins. Such method may utilise the reaction of sialidases and galactose oxidase to produce reactive aldehyde groups that can be chemically conjugated to nucleophilic reactive groups to attach a polymer to a glycoprotein. Such methods may be used to attach a heparosan polymer to a Factor VII glycoprotein. A suitable Factor VII polypeptide for use in such methods may be any Factor VII glycopeptide that comprises terminal galactose. Such a glycoprotein may be produced by treatment of a Factor VII polypeptide with sialidase to remove terminal sialic acid.

WO2011012850 describes the attachment of polymeric groups to a glycosyl group in a glycoprotein. Such methods may be used in accordance with the present invention to attach a heparosan polymer to a Factor VII polypeptide.

Heparosan may be attached to the polypeptide via an engineered extra cysteine in the polypeptide or an exposed sulfhydryl group. The sulfhydryl cysteine group may be coupled to a functionalised heparosan polymer, such as a maleimide-heparosan polymer to obtain a heparosan-polypeptide conjugate.

In one aspect the heparosan polymer is attached to a FVII polypeptide by conjugation to a cysteine on the FVII molecule. The cysteine may be engineered into a Factor VII polypeptide, such as added to the amino acid sequence of a wild-type Factor VII polypeptide. The cysteine may be positioned at the C-terminal of the Factor VII polypeptide, such as at position 407, or in chain at a surface exposed position that will not seriously impede tissue factor binding, FX binding or binding to phospholipids.

In a Factor VII polypeptide that has been modified by addition of a cysteine residue at position 407, the Cys407 can act as site of attachment of a heparosan polymer (e.g. a 13 kDa, 27 kDa, 40 kDa, 52 kDa, 60 kDa, 65 kDa, 108 kDa or 157 kDa heparosan polymer that has been functionalised with maleimide).

As set out in the Examples, a Factor VII polypeptide with unblocked cysteine, such as FVIIa-407C, may be reacted with HEP-maleimide in a suitable buffer such as HEPES and at near neutral pH. The reaction may be allowed to stand at room temperature for, for example, 3-4 hours. Such a reaction can achieve the conjugation of the heparosan polymer to the Factor VII polypeptide.

Factor VII-heparosan conjugates may be purified once they have been produced. For example, purification may comprise by affinity chromatography using immobilised mAb directed towards the Factor VII polypeptide, such as mAb directed against the calcified gla-domain on FVIIa. In such an affinity chromatography method, unconjugated HEP-maleimide may be removed by extensive washing of the column. FVII may be released from the column by releasing the FVII from the antibody. For example, where the antibody is specific to the calcified gla-domain, release from the column may be achieved by washing with a buffer comprising EDTA.

Size exclusion chromatography may be used to separate Factor VII-heparosan conjugates from unconjugated Factor VII.

Pure conjugate may be concentrated by ultrafiltration.

Final concentrations of Factor VII-heparosan conjugate resulting from a process of production may be determined by, for example, HPLC quantification, such as HPLC quantification of the FVII light chain.

Properties of FVII-HEP Conjugates

A conjugate of the invention may show various advantages. For example, the conjugate may show one of more of the following advantages when compared to a suitable control Factor VII molecule.

improved circulating half-life in vivo,
improved mean residence time in vivo
improved biological activity when measured in a proteolysis assay, such as an in vitro proteolysis assay as described herein,
improved biological activity when measured in a clotting assay,
improved biological activity when measured in an in vitro hydrolysis assay as described herein,
improved biological activity when measured in a tissue factor binding assay
improved biological activity when measured in a thrombin generating assay
improved ability to generate Factor Xa.

The conjugate may show an improvement in any biological activity of Factor VII as described herein and this may be measured using any assay or method as described herein, such as the methods described above in relation to the activity of Factor VII.

Advantages may be seen when a conjugate of the invention, i.e. a conjugate of interest, is compared to a suitable control Factor VII molecule. The control molecule may be, for example, an unconjugated Factor VII polypeptide or a conjugated Factor VII polypeptide. The conjugated control may be a FVIIa polypeptide conjugated to a water soluble polymer, or a FVIIa polypeptide chemically linked to a protein.

A conjugated Factor VII control may be a Factor VII polypeptide that is conjugated to a chemical moiety (being protein or water soluble polymer) of a similar size as the heparosan molecule in the conjugate of interest. The water-soluble polymer can for example be polyethylene glycol (PEG), branched PEG, dextran, poly(1-hydroxymethylethylene hydroxymethylformal), 2-methacryloyloxy-2'-ethyltrimethylammoniumphosphate (MPC).

The Factor VII polypeptide in the control Factor VII molecule is preferably the same Factor VII polypeptide that is present in the conjugate of interest. For example, the control Factor VII molecule may have the same amino acid sequence as the Factor VII polypeptide in the conjugate of interest. The control Factor VII may be the same glycosylation pattern as the Factor VII polypeptide in the conjugate of interest.

For example, where the conjugate comprises Factor VII having an additional cysteine at position 407 and the heparosan polymer is attached to that additional cysteine, then the control Factor VII molecule is preferably the same Factor VII molecule having an additional cysteine at position 407, but having no heparosan attached.

Where the activity being compared is the circulating half-life, the control being used for comparison may be a suitable Factor VII conjugated molecule as described above. The conjugate of the invention preferably shows an improvement in circulating half-life, or in mean residence time when compared to a suitable control.

Where the activity being compared is a biological activity of Factor VII, such as clotting activity or proteolysis, the control is preferably a suitable Factor VII polypeptide conjugated to a water soluble polymer of comparable size to the heparosan conjugate of the current invention.

The conjugate may not retain the level of biological activity seen in Factor VII that is not modified by the addition of heparosan. Preferably the conjugate of the invention retains as much of the biological activity of unconjugated Factor VII as possible. For example, the conjugate may retain at least 15%, at least 20%, at least 25%, at least 30%, at least 35%, at least 40%, at least 45%, at least 50% or at least 60% of the biological activity of an unconjugated Factor VII control. As discussed above, the control may be a Factor VII molecule having the same amino acid sequence as the Factor VII polypeptide in the conjugate, but lacking heparosan. The conjugate may, however, show an improvement in biological activity when compared to a suitable control. The biological activity here may be any biological activity of Factor VII as described herein such as clotting activity or proteolysis activity.

An improved biological activity when compared to a suitable control as described herein may be any measurable or statistically significant increase in a biological activity. The biological activity may be any biological activity of Factor VII as described herein, such as clotting activity, proteolysis activity. The increase may be, for example, an increase of at least 5%, at least 10%, at least 15%, at least 20%, at least 25%, at least 30%, at least 35%, at least 40%, at least 45%, at least 50%, at least 55%, at least 60%, at least 70% or more in the relevant biological activity when compared to the same activity in a suitable control.

An advantage of the conjugates of the invention is that heparosan polymers are enzymatically biodegradable. A conjugate of the invention is therefore preferably enzymatically degradable in vivo and/or in vitro.

An advantage of the conjugates of the invention may be that a heparosan polymer linked to Factor VII may reduce or not create inter-assay variability in aPTT-based assays.

Compositions and Formulations

In another aspect, the present invention provides compositions and formulations comprising conjugates of the invention. For example, the invention provides a pharmaceutical composition comprising one or more conjugates of the invention, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. The compositions for parenteral administration comprise the Factor VII conjugate of the invention in combination with, preferably dissolved in, a pharmaceutically acceptable carrier, preferably an aqueous carrier. A variety of aqueous carriers may be used, such as water, buffered water, 0.4% saline, 0.3% glycine and the like. The Factor VII conjugate of the invention can also be formulated into liposome preparations for delivery or targeting to the sites of injury. Liposome preparations are generally described in, e.g., U.S. Pat. Nos. 4,837,028, 4,501,728, and 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of Factor VII conjugate in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected. Thus, a typical pharmaceutical composition for intravenous infusion can be made up to contain 250 ml of sterile Ringer's solution and 10 mg of the Factor VII conjugate. Actual methods for preparing parenterally administrable compositions will be known or apparent to those skilled in the art and are described in more detail in, for example, Remington's Pharmaceutical Sciences, 18th ed., Mack Publishing Company, Easton, Pa. (1990).

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. conjugate) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. The composition should be sterile and should be fluid to the extent that easy syringability exists. It should be stable under the conditions of manufacture and storage and may be preserved against the contaminating action of microorganisms such as bacteria and fungi. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

The conjugate may be used in conjunction with a solvent or dispersion medium containing, for example, water, ethanol, polyol (for example, glycerol, propylene glycol, and liquid poly[ethylene glycol], and the like), suitable mixtures thereof, vegetable oils, and combinations thereof.

The proper fluidity of the conjugate may be maintained, for example, by the use of a coating such as lecithin, by the maintenance of the required particle size in the case of dispersion, and/or by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Sterile injectable solutions may be prepared by incorporating the conjugate in the required amount in an appropriate solvent with one or a combination of ingredients enumerated above, as required, followed by filtered sterilization. Generally, dispersions are prepared by incorporating the heparosan conjugate into a sterile carrier that contains a basic dispersion medium and the required other ingredients from those enumerated above. In the case of sterile powders for the preparation of sterile injectable solutions, the methods of preparation may include vacuum drying, spray drying, spray freezing and freeze-drying that yields a powder of the active ingredient (i.e., the heparosan conjugate) plus any additional desired ingredient from a previously sterile-filtered solution thereof.

Compositions may be formulated in dosage unit form for ease of administration and uniformity of dosage. Dosage unit form as used herein refers to physically discrete units suited as unitary dosages for the subjects to be treated; each unit containing a predetermined quantity of conjugate calculated to produce the desired therapeutic effect. The specification for the dosage unit forms of the presently claimed and disclosed invention(s) are dictated by and directly dependent on (a) the unique characteristics of the heparosan conjugate and the particular therapeutic effect to be achieved, and (b) the limitations inherent in the art of compounding such a therapeutic compound for the treatment of a selected condition in a subject.

Pharmaceutical compositions of the invention may comprise additional active ingredients as well as a conjugate of the invention. For example, a pharmaceutical composition may comprise additional therapeutic or prophylactic agents. For example, where a pharmaceutical composition of the invention is intended for use in the treatment of a bleeding disorder, it may additionally comprise one or more agents intended to reduce the symptoms of the bleeding disorder. For example, the composition may comprise one or more additional clotting factors. The composition may comprise one or more other components intended to improve the condition of the patient. For example, where the composition is intended for use in the treatment of patients suffering from unwanted bleeding such as patients undergoing surgery or patients suffering from trauma, the composition may comprise one or more analgesic, anaesthetic, immunosuppressant or anti-inflammatory agents.

The composition may be formulated for use in a particular method or for administration by a particular route. A conjugate or composition of the invention may be administered parenterally, intraperitoneally, intraspinally, intravenously, intramuscularly, intravaginally, subcutaneously, intranasally, rectally, or intracerebrally.

An advantageous property of the Factor VII polypeptide and heparosan polymer conjugate, of the invention, is where the polymer has a polymer size around in the range of 13-65 kDa (e.g. 13-55 kDa, 25-55 kDa, 25-50 kDa, 25-45 kDa, 30-45 kDa or 38-42 kDa) this may allow for an in vivo useful half-life or mean residence time while also having a suitable viscosity in liquid solution.

Uses of the Conjugates

A conjugate of the invention may be administered to an individual in need thereof in order to deliver Factor VII to that individual. The individual may be any individual in need of Factor VII.

The Factor VII conjugates according to the present invention may be used to control bleeding disorders which may be caused by, for example, clotting factor deficiencies (e.g. haemophilia A and B or deficiency of coagulation factors XI or VII) or clotting factor inhibitors, or they may be used to control excessive bleeding occurring in subjects with a normally functioning blood clotting cascade (no clotting factor deficiencies or inhibitors against any of the coagulation factors). The bleeding may be caused by a defective platelet function, thrombocytopenia or von Willebrand's disease. They may also be seen in subjects in whom an increased fibrinolytic activity has been induced by various stimuli.

For treatment in connection with deliberate interventions, the Factor VII conjugates of the invention will typically be administered within about 24 hours prior to performing the intervention, and for as much as 7 days or more thereafter. Administration as a coagulant can be by a variety of routes as described herein.

The dose of the Factor VII conjugates delivers from about 0.05 mg to 500 mg of the Factor VII polypeptide/day, preferably from about 1 mg to 200 mg/day, and more preferably from about 10 mg to about 175 mg/day for a 70 kg subject as loading and maintenance doses, depending on the weight of the subject and the severity of the condition. A suitable dose may also be adjusted for a particular conjugate of the invention based on the properties of that conjugate, including its in vivo half-life or mean residence time and its biological activity. For example, conjugates having a longer half-life may be administered in reduced dosages and/or compositions having reduced activity compared to wild-type Factor VII may be administered in increased dosages.

The compositions containing the Factor VII conjugates of the present invention can be administered for prophylactic and/or therapeutic treatments. In therapeutic applications, compositions are administered to a subject already suffering from a disease, such as any bleeding disorder as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject. In general, however, the effective delivery amount will range from about 0.05 mg up to about 500 mg of the Factor VII polypeptide per day for a 70 kg subject, with dosages of from about 1.0 mg to about 200 mg of the Factor VII being delivered per day being more commonly used.

The conjugates of the present invention may generally be employed in serious disease or injury states, that is, life threatening or potentially life threatening situations. In such cases, in view of the minimisation of extraneous substances and general lack of immunogenicity of human Factor VII polypeptide variants in humans, it may be felt desirable by the treating physician to administer a substantial excess of these Factor VII conjugate compositions. In prophylactic applications, compositions containing the Factor VII conjugate of the invention are administered to a subject susceptible to or otherwise at risk of a disease state or injury to enhance the subject's own coagulative capability. Such an amount is defined to be a "prophylactically effective dose." In prophylactic applications, the precise amounts of Factor VII polypeptide being delivered once again depend on the subject's state of health and weight, but the dose generally ranges from about 0.05 mg to about 500 mg per day for a 70-kilogram subject, more commonly from about 1.0 mg to about 200 mg per day for a 70-kilogram subject.

Single or multiple administrations of the compositions can be carried out with dose levels and patterns being selected by the treating physician. For ambulatory subjects requiring daily maintenance levels, the Factor VII polypeptide conjugates may be administered by continuous infusion using e.g. a portable pump system.

Local delivery of a Factor VII conjugate of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of Factor VII conjugate sufficient to effectively treat the subject.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Abbreviations used in example 1 to 10:
CMP: Cytidine monophosphate
EDTA: Ethylenediaminetetraacetic acid
Gla: Gamma-carboxyglutamic acid
GlcUA: glucuronic acid
GlcNAc: N-acetylglucosamine
Grx2: glutaredoxin II
GSC: 5'-glycylamidoneuraminic acid cytidine monophosphate
GSC-SH: 5'-[(4-mercaptobutanoyl)glycylamido]neuraminic acid cytidine monophosphate
GSH: Glutathione GSSG: Glutathione disulfide
HEP: HEParosan polymer
HEP-GSC: GSC-functionalized heparosan polymers
HEP-[C]-FVIIa407C: HEParosan conjugated via cysteine to FVIIa407C.
HEP-[N]-FVIIa: HEParosan conjugated via N-glycan to FVIIa.
HEPES: 2-[4-(2-hydroxyethyl)piperazin-1-yl]ethanesulfonic acid
His: Histidine
PmHS1: *Pasteurella mutocida* Heparosan Synthase I
sTF: soluble Tissue Factor
TCEP: Tris(2-carboxyethyl)phosphine
UDP: Uridine diphosphate
Quantification Method:

The conjugates of the invention were analysed for purity by HPLC. HPLC was also used to quantify amount of isolated conjugate based on a FVIIa reference molecule. Samples were analysed either in non-reduced or reduced form. A Zorbax 300SB-C3 column (4.6×50 mm; 3.5 urn Agilent, Cat. No.: 865973-909) was used. Column was operated at 30° C. 5 ug sample was injected, and column eluted with a water (A)—acetonitrile (B) solvent system containing 0.1% trifluoroacetic acid. The gradient program was as follows: 0 min (25% B); 4 min (25% B); 14 min (46% B); 35 min (52% B); 40 min (90% B); 40.1 min (25% B). Reduced samples were prepared by adding 10 ul TCEP/formic acid solution (70 mM tris(2-carboxyethyl)phosphine and 10% formic acid in water) to 25 ul/30 ug FVIIa (or conjugate). Reactions were left for 10 minutes at 70° C., before analysis on HPLC (5 ul injection).

SDS-PAGE Analysis:

SDS PAGE analysis was performed using precast Nupage 7% tris-acetate gel, NuPage tris-acetate SDS running buffer and NuPage LDS sample buffer all from Invitrogen. Samples were denaturized (70° C. for 10 min.) before analysis. HiMark HMW (Invitrogen) was used as standard. Electrophoresis was run in XCell Surelock Complete with power station (Invitrogen) for 80 min at 150 V, 120 mA. Gels were stained using SimplyBlue SafeStain from Invitrogen.

Preparation of HEP-Maleimide Polymers

Maleimide functionalized heparosan polymers of defined size are prepared by an enzymatic (PmHS1) polymerization reaction using the two sugar nucleotides UDP-GlcNAc and UDP-GlcUA. A priming trisaccharide (GlcUA-GlcNAc-GlcUA)NH$_2$ is used for initiating the reaction, and polymerization is run until depletion of sugar nucleotide building blocks. The terminal amine (originating from the primer) is then functionalized with suitable reactive group, in this case a maleimide functionality designed for conjugation to free cysteines. Size of heparosan polymers can be pre-determined by variation in sugar nucleotide: primer stoichiometry. The technique is described in detail in US 2010/0036001.

Example 1

Selective Reduction of FVIIa407C

FVIIa407C was reduced as described in US 20090041744 using a glutathione based redox buffer system. Non-reduced FVIIa 407C (15.5 mg) was incubated for 17h at room temperature in a total volume of 41 ml 50 mM Hepes, 100 mM NaCl, 10 mM CaCl2, pH 7.0 containing 0.5 mM GSH, 15 uM GSSG, 25 mM p-aminobenzamidine and 3 µM Grx2. The reaction mixture was then cooled on ice, and added 8.3 ml 100 mM EDTA solution while keeping pH at 7.0. The entire content was then loaded onto a 5 ml HiTrap Q FF column (Amersham Biosciences, GE Healthcare) equilibrated in buffer A (50 mM Hepes, 100 mM NaCl, 1 mM EDTA, pH 7.0) to capture FVIIa 407C. After wash with buffer A to remove unbound glutathione buffer and Grx2, FVIIa 407C was eluted in one step with buffer B (50 mM Hepes, 100 mM NaCl, 10 mM CaCl2, pH 7.0). The concentration of FVIIa 407C in the eluate was determined by HPLC. 12.6 mg of single cysteine reduced FVIIa407C was isolated in 50 mM Hepes, 100 mM NaCl, 10 mM CaCl2, pH 7.0.

Example 2

Synthesis of 40k HEP-[C]-FVIIa 407C

Single cysteine reduced FVIIa 407C (25 mg) was reacted with 40K HEP-maleimide (26.8 mg) in 50 mM Hepes, 100 mM NaCl, 10 mM CaCl2, pH 7.0 buffer (8.5 ml) for 22 hours at 5° C. The reaction mixture was then loaded on to a FVIIa specific affinity column (CV=64 ml) modified with a Gla-domain specific antibody and step eluted first with 2 column volumes of buffer A (50 mM Hepes, 100 mM NaCl, 10 mM CaCl2, pH 7.4) then two column volumes of buffer B (50 mM Hepes, 100 mM NaCl, 10 mM EDTA, pH 7.4). The method essentially follows the principle described by Thim, L et al. Biochemistry (1988) 27, 7785-779. The products with unfolded Gla-domain was collected and directly applied to a 3×5 ml HiTrap Q FF ion-exchange column (Amersham Biosciences, GE Healthcare, CV=15 ml) equilibrated with 10 mM His, 100 mM NaCl, pH 7.5. The column was washed with 4 column volumes of 10 mM His, 100 mM NaCl, pH 7.5 and 15 column volumes of 10 mM His, 100 mM NaCl, 10 mM CaCl2, pH=7.5 to eluted unmodified FVIIa 407C. The pH was then lowered to 6.0 with 10 mM His, 100 mM NaCl, 10 mM CaCl2, pH=6.0 (12 column volumes). 40k-HEP-[C]-FVIIa407C was eluted with 15 column volumes of a 60% A (10 mM His, 100 mM NaCl, 10 mM CaCl2, pH=6.0) and 40% B (10 mM His, 1 M NaCl, 10 mM CaCl2, pH=6.0) buffer mixture. Fractions containing conjugate were combined, and dialyzed against 10 mM His, 100 mM NaCl, 10 mM CaCl2, pH=6.0 using a Slide-A-Lyzer cassette (Thermo Scientific) with a cut-off of 10 kD. The final volume was adjusted to 0.4 mg/ml (8 uM) by addition of 10 mM His, 100 mM NaCl, 10 mM CaCl2, pH=6.0. Yield (16.1 mg, 64%) was determined by quantifying the FVIIa light chain content against a FVIIa standard after TCEP reduction using reverse phase HPLC.

Example 3

Synthesis of 65k-HEP-[C]-FVIIa407C

FVIIa 407C (8 mg) was reacted with 65 k HEP-maleimide (42 mg 1:4 ratio) in 50 mM Hepes, 100 mM NaCl, 10 mM CaCl$_2$, pH 7.0 buffer (8 ml) for 3 hours at room temperature. The reaction mixture was then applied to a FVIIa specific affinity column (CV=24 ml) modified with a Gla-domain specific antibody and step eluted first with buffer A (50 mM Hepes, 100 mM NaCl, 10 mM CaCl$_2$, pH 7.4) then buffer B (50 mM Hepes, 100 mM NaCl, 10 mM EDTA, pH 7.4). The method essentially follows the principle described by Thim, L et al. Biochemistry (1988) 27, 7785-779. The products with unfolded Gla-domain was collected and directly applied to a HiTrap Q FF ion-exchange column (Amersham Biosciences, GE Healthcare) equilibrated with 10 mM His, 100 mM NaCl, pH 7.5. Unmodified FVIIa 407C was eluted with 5 column volumes of 10 mM His, 100 mM NaCl, 10 mM CaCl2, pH=7.5. The pH was then lowered to 6.0 with 2 column volumes of 10 mM His, 100 mM NaCl, 10 mM CaCl2, pH=6.0. 65k-HEP-[C]-FVIIa407C was eluted using a linear gradient using buffer A (10 mM His, 100 mM NaCl, 10 mM CaCl2, pH=6.0) and buffer B (10 mM His, 1 M NaCl, 10 mM CaCl2, pH=6.0). The gradient was 0-100% B buffer over 10 column volumes, at a flow of 0.5 ml/min. The 65k-HEP-[C]-FVIIa 407C was eluted in approximately 10 mM histidine, ~300 mM NaCl, 10 mM $CaCl_2$, 0.01% Tween80, pH 6.0. Yield and concentration was determined by quantifying the FVIIa light chain content against a FVIIa standard after tris(2-carboxyethyl)-phosphine reduction using reverse phase HPLC. A total of 3.10 mg (38%) 65k-HEP-[C]-FVIIa 407C conjugate was obtained in a concentration of 0.57 mg/ml in 10 mM His, ~300 mM NaCl, 10 mM $CaCl_2$, 0.01% Tween80, pH 6.0. The pure conjugate was finally diluted to 0.4 mg/ml (8 uM) by ultrafiltration, and buffer exchange into 10 mM Histidine, 100 mM NaCl, 10 mM $CaCl_2$, 0.01% Tween 80, pH 6.0 by dialysis.

Example 4

Synthesis of 13k-HEP-[C]-FVIIa407C

This conjugate was prepared as described in example 2, using FVIIa 407C (17 mg) and 13k-HEP-maleimide (8.5 mg). 7.1 mg (41%) 13k-HEP-[C]-FVIIa407C was obtained as a 0.4 mg/ml (8 uM) solution in 10 mM Histidine, 100 mM NaCl, 10 mM $CaCl_2$, 0.01% Tween 80, pH 6.0.

Example 5

Synthesis of 27k-HEP-[C]-FVIIa407C

This conjugate was prepared as described in example 2, using FVIIa 407C (15.7 mg) and 27k-HEP-maleimide (11.2 mg). 6.9 mg (44%) 27k-HEP-[C]-FVIIa407C was obtained as a 0.4 mg/ml (8 uM) solution in 10 mM Histidine, 100 mM NaCl, 10 mM $CaCl_2$, 0.01% Tween 80, pH 6.0.

Example 6

Synthesis of 52k-HEP-[C]-FVIIa407C

This conjugate was prepared as described in example 2, using FVIIa 407C (8.3 mg) and 52k-HEP-maleimide (27 mg). 6.15 mg (71%) 52k-HEP-[C]-FVIIa407C was obtained as a 0.4 mg/ml (8 uM) solution in 10 mM Histidine, 100 mM NaCl, 10 mM $CaCl_2$, 0.01% Tween 80, pH 6.0.

Example 7

Synthesis of 60k-HEP-[C]-FVIIa407C

This conjugate was prepared as described in example 2, using FVIIa 407C (14.3 mg) and 60k-HEP-maleimide (68 mg). 8.60 mg (60%) 60k-HEP-[C]-FVIIa407C was obtained as a 0.4 mg/ml (8 uM) solution in 10 mM Histidine, 100 mM NaCl, 10 mM $CaCl_2$, 0.01% Tween 80, pH 6.0.

Example 8

Synthesis of 108k-HEP-[C]-FVIIa407C

This conjugate was prepared as described in example 2, using FVIIa 407C (20.0 mg) and 108k-HEP-maleimide (174 mg). 3.75 mg (19%) 108k-HEP-[C]-FVIIa407C was obtained as a 0.4 mg/ml (8 uM) solution in 10 mM Histidine, 100 mM NaCl, 10 mM $CaCl_2$, 0.01% Tween 80, pH 6.0.

Example 9

Synthesis of 157k-HEP-[C]-FVIIa407C

This conjugate was prepared as described in example 2, using FVIIa 407C (14.5 mg) and 157k-HEP-maleimide (180 mg). 4.93 mg (34%) 157k-HEP-[C]-FVIIa407C was obtained as a 0.3 mg/ml (6 uM) solution in 10 mM Histidine, 100 mM NaCl, 10 mM $CaCl_2$, 0.01% Tween 80, pH 6.0.

Example 10

Synthesis of Glycoconjugated 52k-HEP-[N]-FVIIa

Step 1: Preparation of 5'-[(4-mercaptobutanoyl)glycylamido]neuraminic acid cytidine monophosphate N-glycyl neuraminic acid cytidine monophosphate (200 mg; 0.318 mmol) was dissolved in water (2 ml), and thiobutyrolactone (325 mg; 3.18 mmol) was added. The two phase solution was gently mixed for 21h at room temperature. The reaction mixture was then diluted with water (10 ml) and applied to a reverse phase HPLC column (C18, 50 mm×200 mm). Column was eluted at a flow rate of 50 ml/min with a gradient system of water (A), acetonitrile (B) and 250 mM ammonium hydrogen carbonate (C) as follows: 0 min (A: 90%, B: 0%, C: 10%); 12 min (A: 90%, B: 0%, C: 10%); 48 min (A: 70%, B: 20%, C: 10%). Fractions (20 ml size) were collected and analysed by LC-MS. Pure fractions were pooled, and passed slowly through a short pad of Dowex 50W×2 (100-200 mesh) resin in sodium form, before lyophilized into dry powder. Content of title material in freeze dried powder was then determined by HPLC using absorbance at 260 nm, and N-glycylneuraminic acid cytidine monophosphate as reference material. For the HPLC analysis, a Waters X-Bridge phenyl column (5 um 4.6 mm×250 mm) and a water acetonitrile system (linear gradient from 0-85% acetonitrile over 30 min containing 0.1% phosphoric acid) was used. Yield: 61.6 mg (26%). LCMS: 732.18 ($MH^+$); 427.14 ($MH^+$-CMP). Compound was stable for extended periods (>12 months) when stored a −80° C.

Step 2: Preparation of 52k-HEP-GSC reagent.The heparosan GSC reagent was prepared by coupling GSC-SH (5'-[(4-mercaptobutanoyl)glycylamido]neuraminic acid cytidine monophosphate) with 52k-HEP-maleimide in a 1:1 molar ratio as follows: GSC-SH (0.50 mg) dissolved in 50 mM Hepes, 100 mM NaCl, pH 7.0 (50 ul) was added 15.80 mg of the 52k-HEP-maleimide dissolved in 50 mM Hepes, 100 mM NaCl, pH 7.0 (1350 ul). The clear solution was left for 2 hours at 25° C. The excess of GSC-SH was removed by dialysis, using a Slide-A-Lyzer cassette (Thermo Scientific) with a cut-off of 10 kD. The dialysis buffer was 50 mM Hepes, 100 mM NaCl, 10 mM CaCl2, pH=7.0. The reaction mixture was dialyzed twice for 2.5 hours. The recovered material was used as such in step 4 below, assuming a quantitative reaction between GSC-SH and HEP-maleimide.

Step 3: Desialylation of FVIIa: FVIIa (28 mg) was added sialidase (*Arthrobacter ureafaciens*, 200 ul, 0.3 mg/ml, 200 U/ml) in 50 mM Hepes, 150 mM NaCl, 10 mM CaCl2, pH 7.0 (18 ml), and left for 1 hour at room temperature. The reaction mixture was then diluted with 50 mM Hepes, 150 mM NaCl, pH 7.0 (30 ml), and cooled on ice. 100 mM EDTA solution (6 ml) was added in small portions. After each addition pH was measured. pH was maintained within 5.5-9.0. The EDTA treated sample was then applied to a 2×5 ml HiTrap Q FF ion-exchange columns (Amersham Biosciences, GE Healthcare) equilibrated with 50 mM Hepes, 150 mM NaCl, pH 7.0. Sialidase was eluted with 50 mM Hepes, 150 mM NaCl, 10 mM CaCl2, pH 7.0 (4 CV), before eluting asialo FVIIa with 50 mM Hepes, 150 mM NaCl, 10 mM CaCl2, pH 7.0 (10 CV). AsialoFVIIa was isolated in 50 mM Hepes, 150 mM NaCl, 10 mM CaCl2, pH 7.0. Yield (24 mg) and concentration (3.0 mg/ml) was determined by quantifying the FVIIa light chain content against a FVIIa standard after tris(2-carboxyethyl)phosphine reduction using reverse phase HPLC.

Step 4: Enzymatic Heparosan Conjugation Using 52k-HEP-GSC reagent: To asialo FVIIa (7.2 mg) in 50 mM Hepes, 150 mM NaCl, 10 mM CaCl2, pH 7.0 (2.5 ml) was added 52 kDa-HEP-GSC (15.8 mg from step 2), and rat ST3GalIII enzyme (1 mg; 1.1 unit/mg) in 20 mM Hepes, 120 mM NaCl, 50% glycerol, pH 7.0 (2 ml). The reaction mixture was incubated for 18 hours at 32° C. under slow stirring. A solution of 157 mM CMP-NAN in 50 mM Hepes, 150 mM NaCl, 10 mM CaCl2, pH 7.0 (0.2 ml) was then added, and the reaction was incubated at 32° C. for an additional hour. HPLC analysis showed a product distribution containing un-reacted FVIIa (70%) and FVIIa conjugated with one heparosan polymer (27%).

Step 5: Isolation of 52k-HEP-[N]-FVIIa: The reaction mixture was then applied to a FVIIa specific affinity column (CV=25 ml) modified with a Gla-domain specific antibody and step eluted first with 2 column volumes of buffer A (50 mM Hepes, 100 mM NaCl, 10 mM $CaCl_2$, pH 7.4) then 2 column volumes of buffer B (50 mM Hepes, 100 mM NaCl, 10 mM EDTA, pH 7.4). The method essentially follows the principle described by Thim, L et al. Biochemistry (1988) 27, 7785-779. The products with unfolded Gla-domain was collected and directly applied to a 5 ml HiTrap Q FF ion-exchange column (Amersham Biosciences, GE Healthcare) equilibrated with a buffer containing 10 mM His, 100 mM NaCl, pH 7.5. The column was washed with 4 column volumes of 10 mM His, 100 mM NaCl, pH=7.5 and 5 column volumes of 10 mM His, 100 mM NaCl, 10 mM CaCl2, pH=7.5 which eluted unmodified FVIIa. The pH was then lowered to 6.0 with 10 mM His, 100 mM NaCl, 10 mM CaCl2, pH=6.0 (4 column volumes). MonoHEPylated FVIIa was eluted with 5 column volumes of 60% A (10 mM His, 100 mM NaCl, 10 mM CaCl2, pH=6.0) and 40% B (10 mM His, 1 M NaCl, 10 mM CaCl2, pH=6.0) buffer mixture. Fractions were combined, and dialyzed against 10 mM His, 100 mM NaCl, 10 mM CaCl2, pH=6.0 using a Slide-A-Lyzer cassette (Thermo Scientific) with a cut-off of 10 kD. The final volume was adjusted to 0.4 mg/ml (8 uM) by addition of 10 mM His, 100 mM NaCl, 10 mM CaCl2, pH=6.0. Yield (1.4 mg) was determined by quantifying the FVIIa light chain content against a FVIIa standard after tris(2-carboxyethyl)phosphine reduction using reverse phase HPLC.

Plasma Analysis:

FVIIa clotting activity levels of 65K HEP-FVIIa 407C conjugates in rat plasma were estimated using a commercial FVIIa specific clotting assay; STACLOT®VIIa-rTF from Diagnostica Stago. The assay is based on the method published by J. H. Morrissey et al, Blood. 81:734-744 (1993). It measures sTF initiated FVIIa activity-dependent time to fibrin clot formation in FVII deficient plasma in the presence of phospholipids. Samples were measured on an ACL9000 coagulation instrument against FVIIa calibration curves with the same matrix as the diluted samples (like versus like). The lower limit of quantification (LLOQ) was estimated to 0.25 U/ml.

Comparable analysis between cysteine conjugated 13 kDa-, 27 kDa-, 40 kDa-, 52 kDa-, 60 kDa-, 65 kDa-, 108 kDa-, 157 kDa-HEP-[C]-FVIIa407C, glycoconjugated 52 kDa-HEP-[N]-FVIIa and reference molecules (40 kDa-PEG-[N]-FVIIa and 40 kDa-PEG-[C]-FVIIa407C) is shown in FIG. 3. From plasma analysis it is found that heparosan conjugated FVIIa analogues has similar or better activity than the PEG-FVIIa reference molecules.

Proteolytic Activity Using Plasma-Derived Factor X as Substrate

The proteolytic activity of the HEP-FVIIa conjugates was estimated using plasma-derived factor X (FX) as substrate. All proteins were diluted in 50 mM Hepes (pH 7.4), 100 mM NaCl, 10 mM $CaCl_2$, 1 mg/mL BSA, and 0.1% (w/v) PEG8000. The kinetic parameters for FX activation were determined by incubating 10 nM of each FVIIa conjugate with 40 nM FX in the presence of 25 µM PC:PS phospholipids (Haematologic technologies) for 30 min at room temperature in a total reaction volume of 100 µL in a 96-well plate (n=2). FX activation in the presence of soluble tissue factor (sTF) was determined by incubating 5 pM of each FVIIa conjugate with 30 nM FX in the presence of 25 µM PC:PS phospholipids for 20 min at room temperature in a total reaction volume of 100 µL (n=2). After incubation, reactions were quenched by adding 50 µL stop buffer [50 mM Hepes (pH 7.4), 100 mM NaCl, 80 mM EDTA] followed by the addition of 50 µL 2 mM chromogenic peptide S-2765 (Chromogenix). Finally, the absorbance increase was measured continuously at 405 nm in a Spectramax 190 microplate reader. Catalytic efficiencies (kcat/Km) were determined by fitting the data to a revised form of the Michaelis Menten equation ([S]<Km) using linear regression. The amount of FXa generated was estimated from a FXa standard curve.

Figure 4:
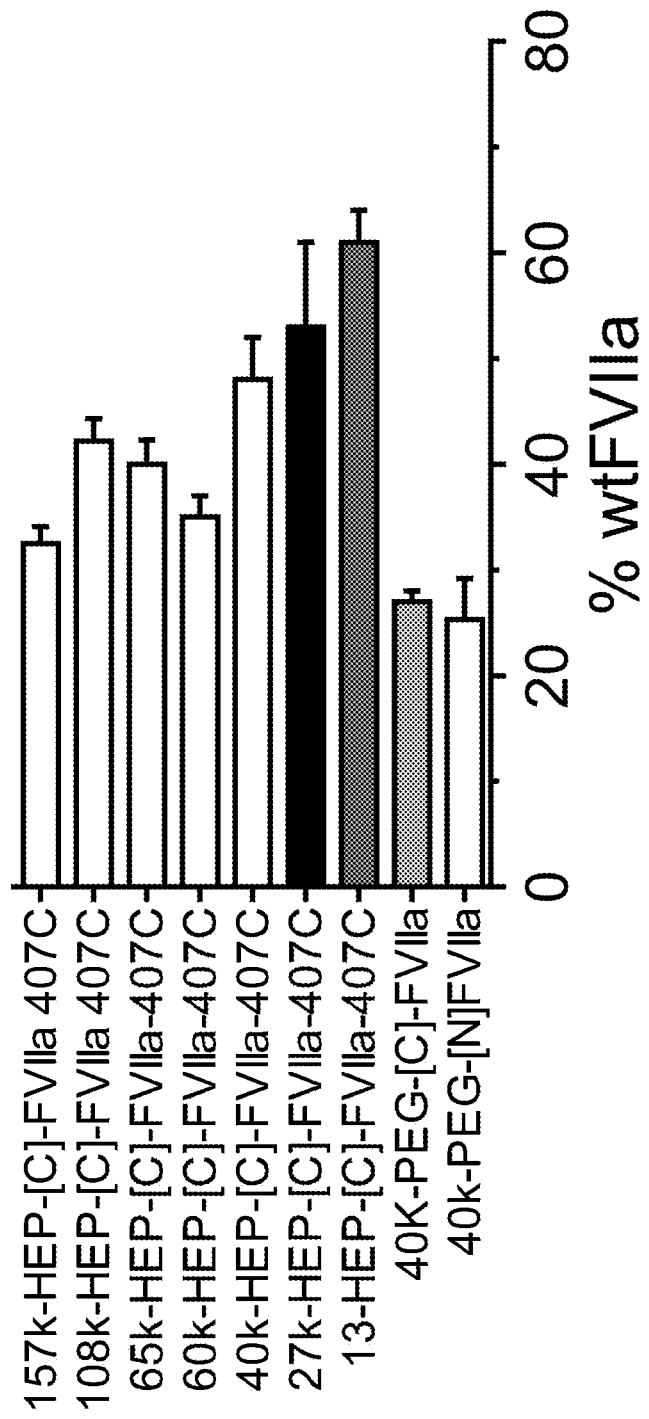
FIG. 4: Proteolytic activity of heparosan conjugates and glycoPEGylated FVIIa references.

Comparable analysis between 13 kDa, 27 kDa, 40 kDa, 60 kDa, 65 kDa, 108 kDa, 157 kDa-HEP-FVIIa 407C and reference molecules (40 kDa-PEG-[N]-FVIIa and 40 kDa-PEG-[C]-FVIIa407C) is shown in FIG. 4.

Surprisingly, it is found that heparosan conjugated FVIIa analogues all are more active than PEG-FVIIa controls in FX activation assay. For some analogues (e.g. 40 kDa-HEP-FVIIa407C), activity is nearly 2 fold higher than for corresponding 40 kDa-PEG analogues.

Pharmacokinetic Evaluation in Sprague Dawley Rats

HEP-FVIIa conjugates were formulated in 10 mM Histidine, 100 mM NaCl, 10 mM $CaCl_2$, 0.01% Tween80 80, pH 6.0. Sprague Dawley rats (three to six per group) were dosed intravenously with 20 nmol/kg test compound. Stabylite™ (TriniLize Stabylite Tubes; Tcoag Ireland Ltd, Ireland) stabilized plasma samples were collected as full profiles at appropriate time points and frozen until further analysis. Plasma samples were analysed for FVIIa clot activity level using a commercial FVIIa specific clotting assay; STACLOT®VIIa-rTF from Diagnostica Stago and antigen concentrations in plasma were determined using LOCI technology.

Figure 5:
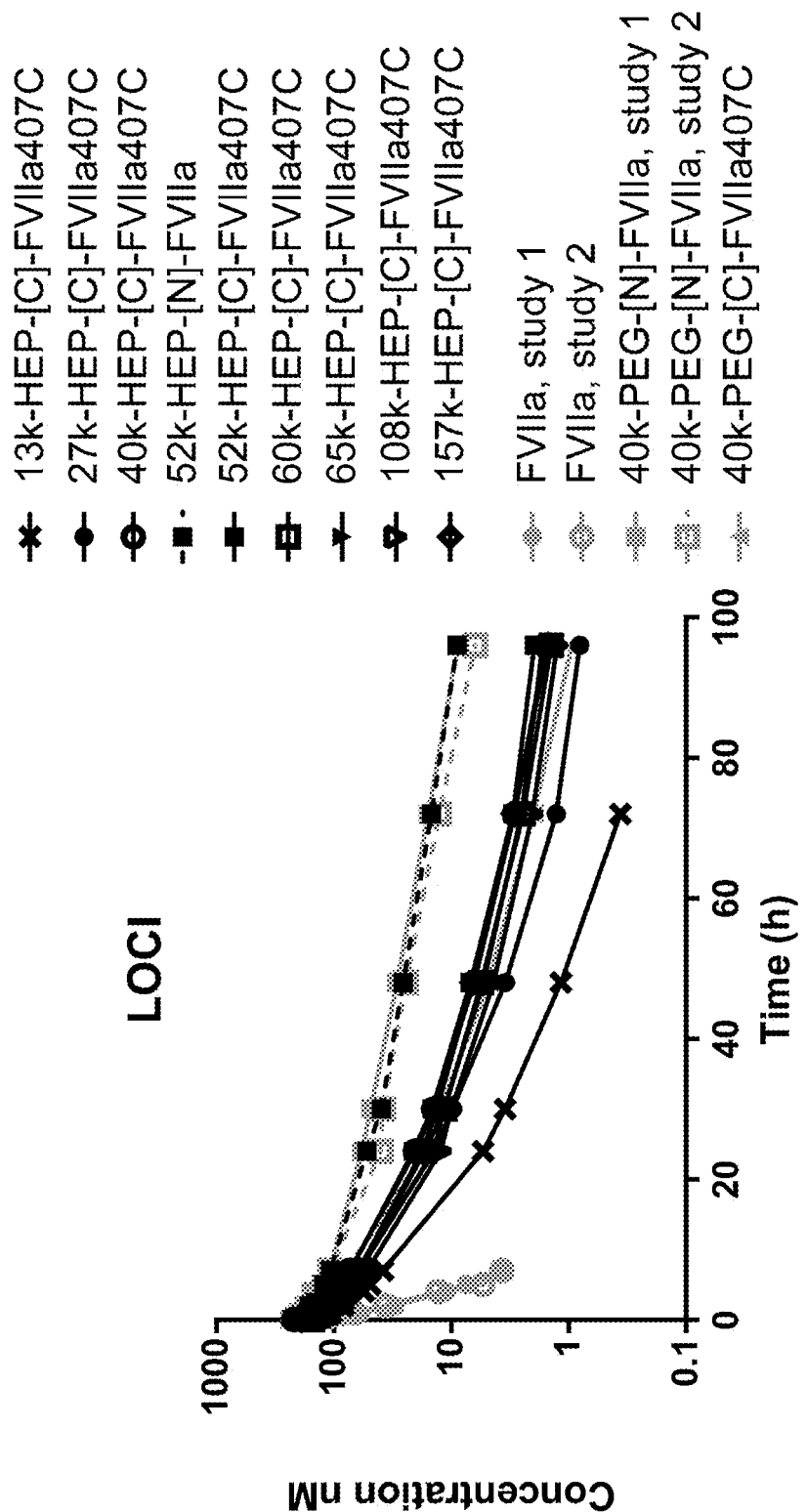
FIG. 5: PK results (LOCI) in Sprague Dawley rats. Comparison of unmodified FVIIa (2 studies), 13k-HEP-[C]-FVIIa407C, 27k-HEP-[C]-FVIIa407C, 40k-HEP-[C]-FVIIa407C, 52k-HEP-[C]-FVIIa407C, 65k-HEP-[C]-FVIIa407C, 108k-HEP-[C]-FVIIa407C and 157k-HEP-[C]-FVIIa407C, glycoconjugated 52k-HEP-[N]-FVIIa and reference molecules (40 kDa-PEG-[N]-FVIIa (2 studies) and 40 kDa-PEG-[C]-FVIIa407C). Data are shown as mean±SD (n=3-6) in a semilogarithmic plot.
Figure 6:
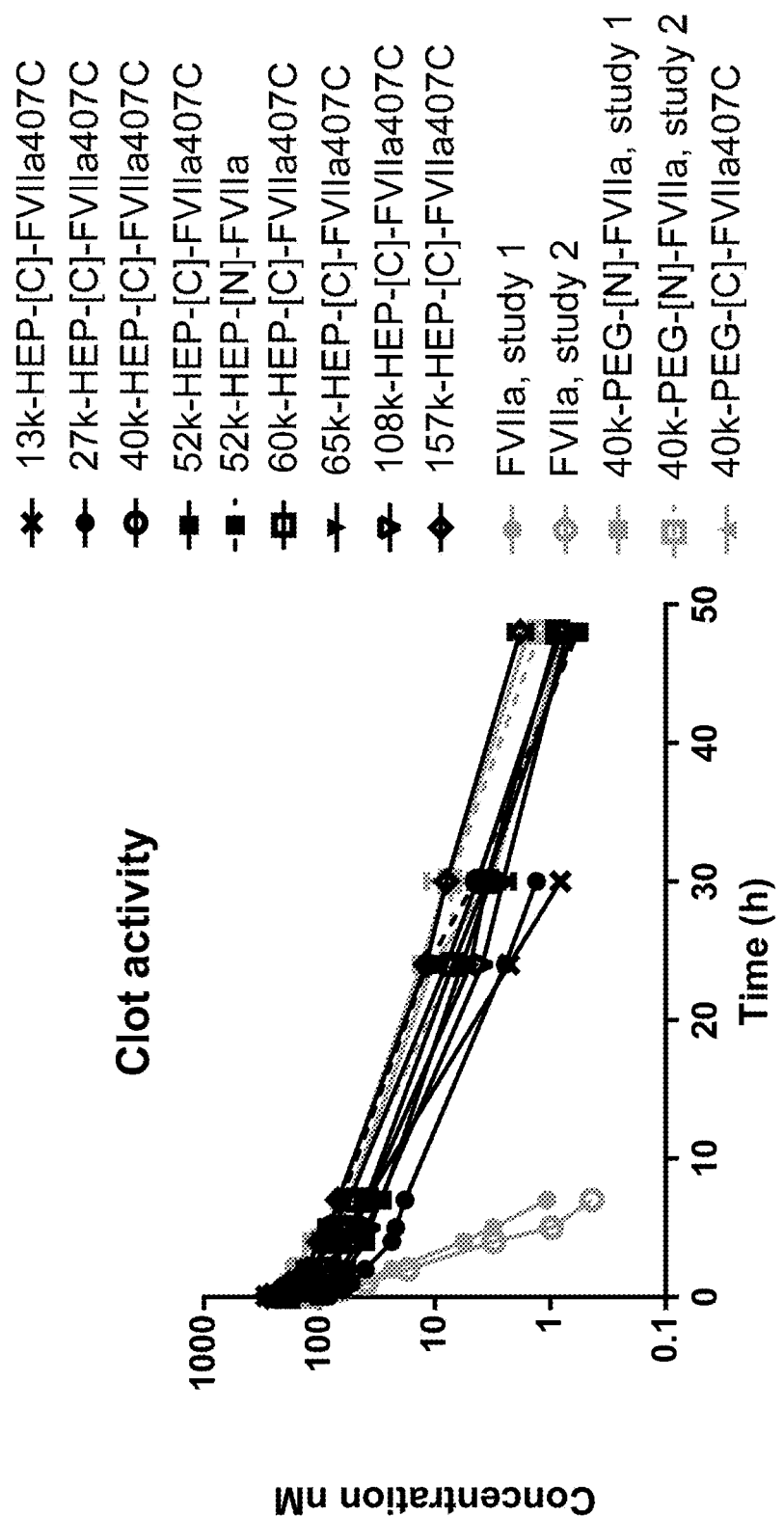
FIG. 6: PK results (Clot Activity) in Sprague Dawley rats. Comparison of unmodified FVIIa (2 studies), 13k-HEP-[C]-FVIIa407C, 27k-HEP-[C]-FVIIa407C, 40k-HEP-[C]-FVIIa407C, 52k-HEP-[C]-FVIIa407C, 65k-HEP-[C]-FVIIa407C, 108k-HEP-[C]-FVIIa407C and 157k-HEP-[C]-FVIIa407C, glycoconjugated 52k-HEP-[N]-FVIIa and reference molecules (40 kDa-PEG-[N]-FVIIa (2 studies) and 40 kDa-PEG-[C]-FVIIa407C). Data are shown in a semilogarithmic plot.

Pharmacokinetic analysis was carried out by non-compartmental methods using Phoenix WinNonlin 6.0 (Pharsight Corporation). The following parameters were estimated: Cmax (maximum concentration) of FVIIa-antithrombin complex, and T½ (the functional terminal half-life) and MRT (the mean residence time) for clot activity. PK-profiles (LOCI and FVIIa:clot) are shown in FIGS. 5 and 6.

A plot of all LOCI based mean-residence times, as obtained from the non-compartmental analysis methods is shown in FIG. 7.

A linear relation is found between HEP-size and MRT around 13-40 kDa size range. A plateau is reached at approximately 40 kDa HEP-size and beyond.

The invention is further described by the following non-limiting embodiments:

In one embodiment the conjugate is composed of a FVII polypeptide and a heparosan polymer.

In one embodiment, the heparosan polymer has a mass of between 5 k and 200 k.

In one embodiment the heparosan polymer has a polydispersity index (Mw/Mn) of less than 1.10

In one embodiment the heparosan polymer has a polydispersity index (Mw/Mn) of less than 1.07

In one embodiment the heparosan polymer has a polydispersity index (Mw/Mn) of less than 1.05

In one embodiment the FVII polypeptide is conjugated to a heparosan polymer having a size of 10 kDa±5 kDa.

In one embodiment the FVII polypeptide is conjugated to a heparosan polymer having a size of 20 kDa±5 kDa In one embodiment the FVII polypeptide is conjugated to a heparosan polymer having a size of 30 kDa±5 kDa.

In one embodiment the FVII polypeptide is conjugated to a heparosan polymer having a size of 40 kDa±5 kDa.

In one embodiment the FVII polypeptide is conjugated to a heparosan polymer having a size of 50 kDa±5 kDa.

In one embodiment, the heparosan polymer is branched via a chemical linker.

In one embodiment, said heparosan polymers each have a size equal to 20 kDa±3 kDa.

In one embodiment, said heparosan polymers each have a size equal to 30 kDa±5 kDa.

In one embodiment, the heparosan polymer is conjugated to FVII polypeptide via an N-glycan.

In one embodiment, one of the two N-glycans at position 145 and 322 are removed by PNGase F treatment, and Heparosan is coupled to the remaining N-glycan.

In another embodiment, the heparosan polymer is conjugated via a sialic acid moiety on FVIIa.

In one embodiment heparosan is coupled to a FVII polypeptide mutant via a single surface exposed cysteine residue.

The invention is further described by the following list of non-limiting embodiments:

Embodiment 1: A conjugate between a Factor VII polypeptide and a heparosan polymer.

Embodiment 2: A conjugate according to embodiment 1 wherein said polymer has a polydispersity index (Mw/Mn) of less than 1.10.

Embodiment 3: A conjugate according to embodiment 1 or 2 wherein said polymer has a size between 5 kDa and 200 kDa.

Embodiment 4: A conjugate according to embodiment 1 or 2 wherein said polymer has a size between (a) 10 kDa and 30 kDa or (b) 30 kDa and 50 kDa or (c) 50 kDa and 70 kDa Embodiment 5: A conjugate according to embodiment 1 or 2 wherein said polymer has a size in a range selected from 5-15 kDa, 15-25 kDa, 25-35 kDa, 35-45 kDa, 45-55 kDa, 55-65 kDa, 65-75 kDa, 75-85 kDa or 85-95 kDa.

Embodiment 6: A conjugate according to embodiment 1 or 2 wherein said polymer has a molecular weight of 20 kDa to 35 kDa, such as 22 kDa to 32 kDa such as 25 kDa to 30 kDa, such as about 27 kDa; or 35 to 65 kDa such as 40 kDa to 60 kDa, such as 47 kDa to 57 kDa, such as 50 kDa to 55 kDa such as about 52 kDa; or 50 to 75 kDa such as 60 to 70 kDa, such as 63 to 67 kDa such as about 65 kDa.

Embodiment 7: A conjugate according to embodiments 1-6 wherein said conjugate has (a) increased circulating half-life compared to the same Factor VII polypeptide which is not conjugated to a heparosan polymer, or (b) increased functional half-life compared to the same Factor VII polypeptide which is not conjugated to a heparosan polymer.

Embodiment 8: A conjugate according to embodiments 1-6 wherein said conjugate has (a) increased mean residence time compared to the same Factor VII polypeptide which is not conjugated to a heparosan polymer, or (b) increased functional mean residence time compared to the same Factor VII polypeptide which is not conjugated to a heparosan polymer.

Embodiment 9: A conjugate according to embodiments 1-8 wherein said Factor VII polypeptide is a Factor VIIa polypeptide.

Embodiment 10: A conjugate according to embodiments 1-9 wherein said Factor VII polypeptide is a mutant Factor VII polypeptide carrying a free cysteine.

Embodiment 11: A conjugate according to embodiments 1-10 wherein said Factor VII polypeptide is FVIIa-407C.

Embodiment 12: A conjugate according to embodiment 11 wherein said heparosan polymer is attached to the cysteine at position 407 of said Factor VII polypeptide.

Embodiment 13: A conjugate according to any one of embodiments 1 to 11 where the polymer is attached to the polypeptide via N- or O-glycans.

Embodiment 14: A pharmaceutical composition comprising a conjugate according to any one of the preceding embodiments and a pharmaceutically acceptable carrier or diluent.

Embodiment 15: A conjugate according to any one of embodiments 1 to 13 or a composition according to embodiment 14 for use in a method of treating or preventing a bleeding disorder.

The invention is further described by the following list of non-limiting but particularly interesting embodiments:

Embodiment 1: A conjugate comprising a Factor VII polypeptide and a heparosan polymer.

Embodiment 2: A conjugate according to embodiment 1, wherein said polymer has a size in a range selected from 13-65 kDa, 13-55 kDa, 25-55 kDa, 25-50 kDa, 25-45 kDa, 30-45 kDa and 38-42 kDa.

Embodiment 3: A conjugate according to embodiment 1, wherein said polymer has a size in a range selected from: 30-50 kDa, 35-65 kDa, 35-45 kDa, 45-55 kDa, 40-60 kDa or 55-65 kDa.

Embodiment 4: A conjugate according to embodiment 2 or 3, wherein said polymer has a molecular weight selected from; 40 kDa±5 kDa, 40 kDa±4 kDa, 40 kDa±3 kDa 40 kDa±2 kDa and 40 kDa±1 kDa.

Embodiment 5: A conjugate according to any one of embodiments 1-4, wherein said polymer has a molecular weight selected from 38 kDa, 39 kDa, 40 kDa, 41 kDa, and 42 kDa.

Embodiment 6: A conjugate according to any one of embodiments 1-5, wherein said polymer has a molecular weight of 40 kDa.

Embodiment 7: A conjugate according to any one of embodiments 1-6, wherein said polymer has a polydispersity index (Mw/Mn) of less than 1.10, 1.09, 1.08, 1.07, 1.06, 1.05, 1.04 or 1.03.

Embodiment 8: A conjugate according to any one of embodiments 1-7, wherein said polymer has a polydispersity index (Mw/Mn) of less than 1.05.

Embodiment 9: A conjugate according to any one of embodiments 1-8, wherein the polymer is attached to the Factor VII polypeptide via an N-glycan.

Embodiment 10: A conjugate according to any one of embodiments 1-8, wherein said Factor VII polypeptide is a mutant Factor VII polypeptide carrying a free cysteine.

Embodiment 11: A conjugate according to embodiment 10, wherein said Factor VII polypeptide is FVIIa-407C.

Embodiment 12: A conjugate according to embodiment 10, wherein said heparosan polymer is attached to the cysteine at position 407 of said Factor VII polypeptide.

Embodiment 13: A conjugate according to any one of the preceding embodiments, wherein said conjugate has
(a) increased circulating half-life compared to the same Factor VII polypeptide which is not conjugated to a heparosan polymer, or
(b) increased functional half-life compared to the same Factor VII polypeptide which is not conjugated to a heparosan polymer.

Embodiment 14: A conjugate according to any one of the preceding embodiments, wherein said conjugate has
(a) increased mean residence time compared to the same Factor VII polypeptide which is not conjugated to a heparosan polymer; or
(b) increased functional mean residence time compared to the same Factor VII polypeptide which is not conjugated to a heparosan polymer.

Embodiment 15: A conjugate according to any one of the previous embodiments, wherein said Factor VII polypeptide is a Factor VIIa polypeptide.

Embodiment 16: A conjugate according to any one of the previous embodiments, wherein the amino acid sequence of the Factor VII polypeptide differs from the sequence of wild-type Factor VII by insertion, deletion, and/or substitution of one or more amino acids.

Embodiment 17: A conjugate according to embodiment 16, wherein the amino acid sequence of the Factor VII polypeptide differs from the sequence of wild-type Factor VII by one, two or three amino acids substitutions.

Embodiment 18: A conjugate according to any one of embodiments 1-11 and 14, wherein said Factor VII polypeptide is human wild-type Factor VIIa.

Embodiment 19: A methods for preparing a conjugate between a Factor VII polypeptide and a heparosan polymer according to any one of the previous embodiments.

Embodiment 20: A pharmaceutical composition comprising a conjugate according to any one of the preceding embodiments and a pharmaceutically acceptable carrier or diluent.

Embodiment 21: A conjugate according to any one of embodiments 1-18 or a composition according to embodiment 18 for use in a method of treating or preventing a bleeding disorder.

The invention claimed is:

1. A conjugate comprising a Factor VII polypeptide and a heparosan polymer;
wherein said heparosan polymer has a size in a range selected from the group consisting of 30-50kDa, 35-65kDa, 35-45kDa, 45-55kDa, 40-60kDa and 55-65kDa; and
wherein said conjugate exhibits at least about 20% more Factor X activation activity in comparison to a conjugate comprising a Factor VII polypeptide and a polyethylene glycol polymer of about the same size.

2. The conjugate according to claim 1, wherein said heparosan polymer has a molecular weight selected from the group consisting of 38kDa, 39kDa, 40kDa, 41kDa, and 42kDa.

3. The conjugate according to claim 1, wherein said heparosan polymer has a polydispersity index (Mw/Mn) of less than 1.10, 1.09, 1.08, 1.07, 1.06, 1.05, 1.04 or 1.03.

4. The conjugate according to claim 1, wherein the heparosan polymer is attached to the Factor VII polypeptide via an N-glycan.

5. The conjugate according to claim 1, wherein said Factor VII polypeptide is a mutant Factor VII polypeptide carrying a free cysteine, and wherein said heparosan polymer is attached to said cysteine.

6. The conjugate according to claim 1, wherein said conjugate has
(a) increased circulating half-life compared to the same Factor VII polypeptide which is not conjugated to a heparosan polymer;
(b) increased functional half-life compared to the same Factor VII polypeptide which is not conjugated to a heparosan polymer;
(c) increased mean residence time compared to the same Factor VII polypeptide which is not conjugated to a heparosan polymer; and/or
(d) increased functional mean residence time compared to the same Factor VII polypeptide which is not conjugated to a heparosan polymer.

7. The conjugate according to claim 1, wherein said Factor VII polypeptide is a Factor VIIa polypeptide.

8. The conjugate according to claim 1, wherein the amino acid sequence of the Factor VII polypeptide differs from the sequence of wild-type Factor VII by insertion, deletion, and/or substitution of one or more amino acids.

9. The conjugate according to claim 8, wherein the amino acid sequence of the Factor VII polypeptide differs from the sequence of wild-type Factor VII by one, two or three amino acids substitutions.

10. The conjugate according to claim 1, wherein said Factor VII polypeptide is human wild-type Factor VIIa.

11. A method for preparing a conjugate according to claim 1, comprising covalently binding a heparosan polymer to an isolated Factor VII polypeptide.

12. A pharmaceutical composition comprising the conjugate according to claim 1 and a pharmaceutically acceptable carrier or diluent.

13. A method for treating or preventing a bleeding disorder, comprising administering the conjugate according to claim 1 to a subject in need thereof.

14. A method for treating or preventing a bleeding disorder, comprising administering the pharmaceutical composition according to claim 12 to a subject in need thereof.

* * * * *